United States Patent [19]

Hung et al.

[11] 4,447,616

[45] May 8, 1984

[54] PYRIDINE CONTAINING BENZOIC ACID DERIVATIVES

[75] Inventors: William M. Hung; Edward E. Ehlinger, both of Cincinnati, Ohio

[73] Assignee: Sterling Drug Inc., New York, N.Y.

[21] Appl. No.: 445,537

[22] Filed: Nov. 30, 1982

[51] Int. Cl.³ .......................................... C07D 213/30
[52] U.S. Cl. .................................. 546/335; 546/15; 546/334; 546/329; 549/344; 346/221
[58] Field of Search ......................................... 546/335

[56] References Cited

U.S. PATENT DOCUMENTS 3,901,918  8/1975  Koga et al. ......................... 260/335
4,032,527  6/1977  Crounse et al. ..................... 546/335

*Primary Examiner*—Robert T. Bond

*Attorney, Agent, or Firm*—Terrence E. Miesle; Paul E. Dupont; B. Woodrow Wyatt

[57] ABSTRACT

2-And/or 6-pyridylethylamino-substituted fluorans useful as color formers, particularly in pressure-sensitive carbonless duplicating systems and thermal-responsive marking systems are prepared by the interaction of (pyridylethylaminophenyl)carbonylbenzoic acids with 4-hydroxy- or alkoxyanilines or by the interaction of (disubstituted aminophenyl)carbonylbenzoic acids with N-pyridylethyl-4-hydroxy- or alkoxy acetanilides. The (pyridylethylaminophenyl)carbonylbenzoic acid intermediates required for the fluorans are prepared by interacting a N-pyridylethyl-3-hydroxyaniline with a substituted or unsubstituted phthalic anhydride. The N-pyridylethyl-4-hydroxy- or alkoxyanilines and the N-pyridylethyl-3-hydroxyanilines are prepared by interacting the respective aniline with a vinylpyridine.

2 Claims, No Drawings

PYRIDINE CONTAINING BENZOIC ACID DERIVATIVES

BACKGROUND OF THE INVENTION (a) Field of the Invention

This invention relates to novel compounds classified in the field of organic chemistry as fluorans useful as color precursors, particularly in the area of carbonless duplicating, for example, pressure-sensitive and thermal-responsive marking systems; to pyridylethyl-substituted anilines and to (pyridylethylaminophenyl)carbonylbenzoic acids useful as intermediates in preparing them; to processes for preparing said fluorans; and to pressure-sensitive duplicating systems and thermal-responsive marking systems containing the same.

(b) Description of the Prior Art

Several classes of organic compounds of widely diverse structural types are known to be useful as colorless precursors for carbonless duplicating systems. Among the more important classes, there may be named phenothiazines, for example, benzoyl leuco methylene blue; phthalides, for example, crystal violet lactone; fluorans, with which this invention is concerned, for example, 2-anilino-6-diethylaminofluoran and 2-dibenzylamino-6-diethylaminofluoran; and various other types of colorless precursors currently employed in commercially accepted carbonless copy systems. Typical of the many such systems taught in the prior art are those described in U.S. Pat. Nos. 2,712,507, 2,800,457 and 3,041,289 which issued July 5, 1955, July 23, 1957 and June 26, 1962, respectively. Many of the color formers in the prior art suffer one or more disadvantages such as low tinctorial strength, poor light stability, low resistance to sublimation, low susceptibility to xerographic copiability of the color-developed form and low solubility in common organic solvents, the latter disadvantage requiring the use of specialized and expensive solvents in order to obtain microencapsulated solutions of sufficient concentration for use in pressure-sensitive copying systems.

The following item to date appears to constitute the most relevant prior art with regard to the instant invention.

U.S. Pat. No. 3,901,918, issued Aug. 26, 1978, discloses novel fluoran compounds such as 2-bis-(5',6',7',8'-tetrahydro-2'-naphthylmethyl)amino-6-diethylaminofluoran and 2-(2'-thenylamino)-8-dimethylbenz[c]fluoran, which are useful as a coloring material for record material systems, such as pressure-sensitive copying paper or heat-sensitive copying paper, wherein colored images are formed by an electron-donor-acceptor color-forming reaction between coloring material and acidic material. This reference teaches, in pertinent part, the species 2-(N-2'-pyridylmethyl-N-acetylamino)-6-dimethylamino-3',4',5'-6'-tetrachlorofluoran.

SUMMARY OF THE INVENTION

The present invention provides for novel fluorans substituted with a pyridylethylamino moiety which are useful as color formers in pressure-sensitive carbonless duplicating systems and in thermal-responsive marking systems. The compounds develop colored images of excellent tinctorial strength and have the advantages of good light stability. The present invention also provides for 2-{N-[2-(pyridyl)ethyl]aminophenyl}carbonylbenzoic acids and N-[2-(pyridyl)ethyl]anilines useful as intermediates to the subject fluoran color formers.

In one of its composition of matter aspects the invention relates to a series of 2-(N-R-N-R$^1$)amino-3-R$^2$-6-(N-R$^3$-N-R$^4$)amino-4'-R$^5$-5'-R$^6$-6'-R$^7$-7'-R$^8$-fluorans which are useful as color formers in pressure-sensitive carbonless duplicating systems and thermal-responsive marking systems.

In a second of its composition of matter aspects, the invention relates to a series of 2-{2-R$^{10}$-4-N-[2-(R$^9$-pyridyl)ethyl]-N-R$^4$-aminophenyl}carbonyl-3-R$^8$-4-R$^7$-5-R$^6$-6-R$^5$-benzoic acids which are useful as intermediates for the preparation of the fluoran final products of the invention.

In a third of its composition of matter aspects, the invention relates to a series of N-[2-(R$^9$-pyridyl)ethyl]N-R$^4$-3-R$^{10}$-N-anilines which, in turn, are useful as intermediates for the preparation of the 2-{2-R$^{10}$-4-N-[2-(R$^9$-pyridyl)ethyl]-N-R$^4$-aminophenyl}carbonyl-3-R$^8$-4-R$^7$-5-R$^6$-6-R$^5$-benzoic acid intermediates of this invention.

In a fourth of its composition of matter aspects, the invention relates to a series of N-[2-(R$^9$-pyridyl)ethyl]-N-R$^1$-4-R$^{11}$-2-R$^2$-anilines which are useful as intermediates for the preparation of the fluoran final products of the invention.

In one of its process aspects, the invention relates to a process for preparing 2-(N-R-N-R$^1$)amino-3-R$^2$-6-(N-R$^3$-N-R$^4$)amino-4'-R$^5$-5'-R$^6$-6'-R$^7$-7'-R$^8$-fluorans which comprises in a first step interacting a 2-{2-R$^{10}$-4-N-[2-(R$^9$-pyridyl)ethyl]-N-R$^4$-aminophenyl}carbonyl-3-R$^8$-4-R$^7$-5-R$^6$-6-R$^5$-benzoic acid with a N-R-N-R$^1$-2-R$^2$-4-R$^{11}$-aniline in the presence of sulfuric acid to obtain a 3-[2-R$^{10}$-4-(N-R$^3$-N-R$^4$)aminophenyl]-3-[2-R$^{11}$-4-R$^2$-5-(N-R-N-R$^1$)aminophenyl]-4-R$^8$-5-R$^7$-6-R$^6$-7-R$^5$-phthalide which in the second step is heated in the presence of an alkali metal hydroxide to obtain the corresponding fluoran.

In a second process aspect, the invention relates to a process for preparing a 2-{2-R$^{10}$-4-N-[2-(R$^9$-pyridyl)ethyl]-N-R$^4$-aminophenyl}carbonyl-3-R$^8$-4-R$^7$-5-R$^6$-6-R$^5$-benzoic acid which comprises interacting a N-[2-(R$^9$-pyridyl)ethyl]-N-R$^4$-3-R$^{10}$-aniline with a 3-R$^5$-4-R$^6$-5-R$^7$-6-R$^8$-phthalic anhydride.

In a third process aspect, the invention relates to a process for preparing a N-[2-(R$^9$-pyridyl)ethyl]-N-R$^1$-4-R$^{11}$-2-R$^2$-aniline which comprises interacting a N-R$^1$-4-R$^{11}$-2-R$^2$-aniline with a R$^9$-vinylpyridine.

In a fourth process aspect, the invention relates to a process for preparing a N-[2-(R$^9$-pyridyl)ethyl]-N-R$^4$-3-R$^{10}$-aniline which comprises interacting a N-R$^4$-3-R$^{10}$-aniline with a R$^9$-vinylpyridine.

In a fifth process aspect, the invention relates to a process for preparing a 2-(N-R-N-R$^1$)amino-3-R$^2$-6-(N-R$^3$-N-R$^4$)-amino-4'R$^5$-5'-R$^6$-6'-R$^7$-7'-R$^8$-fluoran, wherein R$^1$ is an acylated, benzoylated or sulfonylated moiety, which comprises acylating, benzoylating or sulfonylating a 2-(N-R-N-R$^1$)-amino-3-R$^2$-6-(N-R$^3$-N-R$^4$)amino-4'-R$^5$-5'-R$^6$-6'-R$^7$-7'-R$^8$-fluoran in which R$^1$ is hydrogen.

In a sixth process aspect, the invention relates to a process for preparing a 2-(N-R-N-R$^1$)amino-3-R$^2$-6-(N-R$^3$-N-R$^4$)amino-5'/6'-COOY-fluoran wherein Y is alkyl, which comprises esterifying the corresponding 2-(N-R-N-R$^1$)amino-3-R$^2$-6-(N-R$^3$-N-R$^4$)amino-5'/6'-carboxy fluoran with an appropriate alkylating agent in the presence of an alkali.

In a seventh process aspect, the invention relates to a process for preparing 2-(N-R-N-$R^1$)amino-3-$R^2$-6-(N-$R^3$-N-$R^4$)amino-4'-$R^5$-5'-$R^6$-6'-$R^7$-7'-$R^8$-fluoran wherein $R^1$ is a substituted carbonyl moiety, which comprises interacting a 2-N-R-amino-3-$R^2$-6-(N-$R^3$-N-$R^4$)amino-4-$R^5$-5-$R^6$-$R^7$-7-$R^8$-fluoran with an appropriate arylisocyanate in the presence of an organic base.

The present invention provides in its article of manufacture aspect, pressure-sensitive carbonless duplicating systems and thermal responsive marking systems each containing at least one color-forming substance comprising a 2-(N-R-N-$R^1$)amino-3-$R^2$-6-(N-$R^3$-N-$R^4$)amino-4'-$R^5$-5'-$R^6$-7'-$R^7$-7'-$R^8$-fluoran.

DETAILED DESCRIPTION INCLUSIVE OF THE PREFERRED EMBODIMENTS

More specifically, this invention in its first composition of matter aspect, resides in novel fluorans, which are particularly useful as colorless precursors in the art of carbonless duplicating and thermal marking and which are 2-(N-R-N-$R^1$)amino-3-$R^2$-6-(N-$R^3$-N-$R^4$)amino-4'-$R^5$-5'-$R^6$-6'-$R^7$-7'-$R^8$-fluorans having the formula

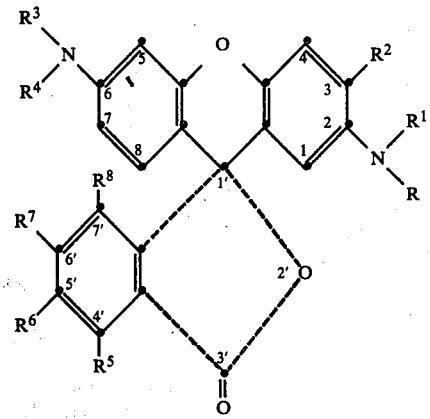

FORMULA I wherein: R and $R^3$ independently represent hydrogen, non-tertiary $C_1$ to $C_8$ alkyl, $C_4$ to $C_8$ cycloalkyl, phenyl, phenyl substituted by one or two of $C_1$ to $C_3$ alkyl, non-tertiary $C_1$ to $C_4$ alkoxy or halo, benzyl, benzyl substituted by one or two of $C_1$ to $C_3$ alkyl, non-tertiary $C_1$ to $C_4$ alkoxy or halo, or

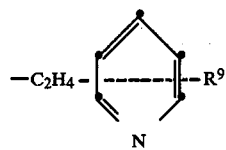

in which $R^9$ represents non-tertiary $C_1$ to $C_4$ alkyl with the proviso that at least one of R and $R^3$ is the 2-($R^9$-pyridyl)ethyl moiety shown above; $R^1$ represents hydrogen, non-tertiary $C_1$ to $C_8$ alkyl, formyl, non-tertiary $C_2$ to $C_4$ acyl, benzoyl, benzoyl substituted in the benzene ring by one or two of halo, non-tertiary $C_1$ to $C_4$ alkyl, non-tertiary $C_1$ to $C_4$ alkoxy or nitro, phenylcarbamyl, naphthylcarbamyl, phenylsulfonyl, phenylsulfonyl substituted in the benzene ring by one or two of halo, non-tertiary $C_1$ to $C_4$ alkyl, non-tertiary $C_1$ to $C_4$ alkoxy or nitro, benzyl or benzyl substituted in the benzene ring by one or two of halo non-tertiary $C_1$ to $C_4$ alkyl, non-tertiary $C_1$ to $C_4$ alkoxy or nitro; $R^2$ represents hydrogen, halo or non-tertiary $C_1$ to $C_4$ alkyl; $R^4$ represents hydrogen, non-tertiary $C_1$ to $C_4$ alkyl, benzyl or benzyl substituted in the benzene ring by one or two of halo, non-tertiary $C_1$ to $C_4$ alkyl, non-tertiary $C_1$ to $C_4$ alkoxy or nitro; $R^3$ and $R^4$ taken together with the nitrogen atom to which they are attached represent pyrrolidino, piperidino or morpholino; $R^5$, $R^6$, $R^7$ and $R^8$ each independently represent hydrogen, halo, nitro, or when $R^5$, $R^8$ and one of $R^6$ and $R^7$ are each hydrogen, the other of $R^6$ and $R^7$ represents COOY in which Y represents hydrogen or non-tertiary $C_1$ to $C_{18}$ alkyl.

In a first particular embodiment in accordance with its first composition of matter aspect, the invention sought to be patented resides in the novel 2-{N-[2-($R^9$-pyridyl)ethyl]-N-$R^1$}amino-3-$R^2$-6-(N-$R^3$-N-$R^4$)amino-4'-$R^5$-5'-$R^6$-6'-$R^7$-7'-$R^8$-fluorans of Formula I wherein R is 2-($R^9$-pyridyl)ethyl according to the formula

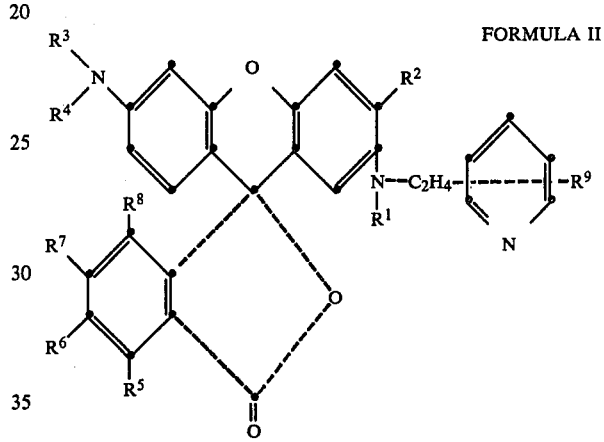

FORMULA II wherein $R^1,R^2,R^3,R^4,R^5,R^6,R^7,R^8$ and $R^9$ each have the same respective meanings given in Formula I. Preferred compounds within the ambit of this particular embodiment are the novel 2-{N-[2-($R^9$-pyridyl)ethyl]-N-$R^1$}amino-3-$R^2$-6-(N-$R^3$-N-$R^4$)amino 4'-$R^5$-5'-$R^6$-$R^7$-7'-$R^8$-fluorans of Formula II wherein $R^1$ represents hydrogen, non-tertiary $C_1$ to $C_8$ alkyl, formyl, non-tertiary $C_2$ to $C_4$ acyl, phenylcarbamyl, naphthylcarbamyl benzyl or benzyl substituted in the benzene ring by one or two of halo, non-tertiary $C_1$ to $C_4$ alkyl, non-tertiary $C_1$ to $C_4$ alkoxy or nitro; $R^2$ represents hydrogen or non-tertiary $C_1$ to $C_4$ alkyl; $R^3$ represents hydrogen, non-tertiary $C_1$ to $C_8$ alkyl, $C_4$ to $C_8$ cycloalkyl, phenyl or phenyl substituted by one or two of $C_1$ to $C_3$ alkyl, non-tertiary $C_1$ to $C_4$ alkoxy or halo; $R^4$ represents hydrogen or non-tertiary $C_1$ to $C_4$ alkyl; $R^3$ and $R^4$ taken together with the nitrogen atom to which they are attached represent pyrrolidino, piperidino or morpholino; and $R^5$, $R^6$, $R^7$ and $R^8$ each represent hydrogen or when $R^5$, $R^8$ and one of $R^6$ and $R^7$ are each hydrogen, the other of $R^6$ and $R^7$ represents COOY in which Y represents hydrogen or non-tertiary $C_1$ to $C_{18}$ alkyl. Particularly preferred compounds within the ambit of this embodiment are: the fluorans of Formula II in which $R^1$ represents hydrogen, non-tertiary $C_1$ to $C_8$ alkyl or benzyl, $R^3$ and $R^4$ each independently represent hydrogen or non-tertiary $C_1$ to $C_4$ alkyl and $R^5$, $R^6$, $R^7$ and $R^8$ each represent hydrogen; are those in which $R^1$ represents hydrogen or non-tertiary $C_1$ to $C_8$ alkyl, $R^3$ and $R^4$ taken together with the nitrogen atom to which they are attached represent pyrrolidino, piperidino or morpholino and $R^5R^6$, $R^7$ and $R^8$ each represent hydrogen; those in which $R^1$ represents formyl or non-tertiary $C_2$ to $C_4$ acyl, $R^3$ and $R^4$ each independently represent hydrogen or non-tertiary $C_1$ to $C_4$ alkyl and $R^5$, $R^6$, $R^7$ and $R^8$ each represent hydrogen; those in which $R^1$ represents phenylcarbamyl or naphthylcarbamyl, $R^3$ and $R^4$ each independently represent hydrogen or non-tertiary $C_1$ to $C_4$ alkyl and $R^5$, $R^6$, $R^7$ and $R^8$ each represent hydrogen; and those in which $R^1$ represents hydrogen or non-tertiary $C_1$ to $C_8$ alkyl, $R^3$ and $R^4$ each independently represent hydrogen or non-tertiary $C_1$ to $C_4$ alkyl and $R^5$, $R^8$ and one of $R^6$ and $R^7$ each represent hydrogen and the other of $R^6$ and $R^7$ represents COOY in which Y represents hydrogen or non-tertiary $C_1$ to $C_{18}$ alkyl.

In a second particular embodiment in accordance with the first composition of matter aspect, the invention sought to be patented resides in novel 2-(N-R-N-$R^1$)amino-3-$R^2$-6-{N-[2-($R^9$-pyridyl)ethyl]-N-$R^4$}amino-4'-$R^5$-5'-$R^6$-6'-$R^7$-7'-$R^8$-fluorans of Formula I wherein $R^3$ is 2-($R^9$-pyridyl)ethyl according to the formula

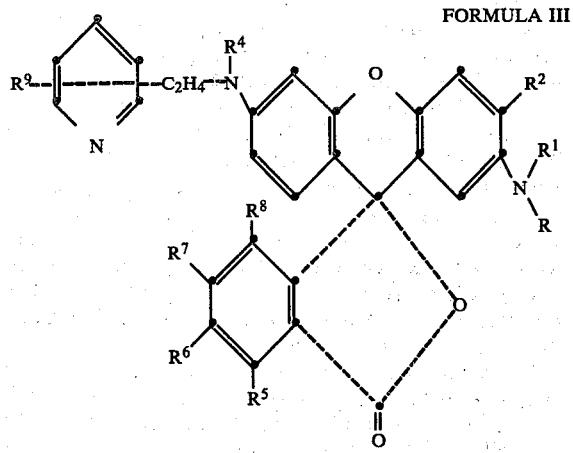

FORMULA III wherein R,$R^1$,$R^2$,$R^4$,$R^5$,$R^6$,$R^7$,$R^8$ and $R^9$ each have the same respective meanings given in Formula I. Preferred compounds within the ambit of the second particular embodiment are the novel 2-(N-R-N-$R^1$)amino-3-$R^2$-6-{N-[2-($R^9$-pyridyl)ethyl]-N-$R^4$}amino-4'-$R^5$-5'-$R^6$-6'-$R^7$-7'-$R^8$-fluorans of Formula III wherein R represents hydrogen, non-tertiary $C_1$ to $C_8$ alkyl, phenyl, phenyl substituted by one or two of $C_1$ to $C_3$ alkyl, non-tertiary $C_1$ to $C_4$ alkoxy or halo, benzyl or benzyl substituted by one or two of $C_1$ to $C_3$ alkyl, non-tertiary $C_1$ to $C_4$ alkoxy or halo; $R^1$ represents hydrogen, non-tertiary $C_1$ to $C_8$ alkyl, benzyl or benzyl substituted by one or two of $C_1$ to $C_3$ alkyl, non-tertiary $C_1$ to $C_4$ alkoxy or halo; $R^2$ represents hydrogen or non-tertiary $C_1$ to $C_4$ alkyl; $R^4$ represents hydrogen or non-tertiary $C_1$ to $C_4$ alkyl; and $R^5$, $R^6$, $R^7$, and $R^8$ each represent hydrogen.

This invention in its second composition of matter aspect, resides in the novel benzoic acids, which are particularly useful as intermediates to the novel fluorans of Formula I and which are 2-{N-[2-($R^9$-pyridyl)ethyl]-N-$R^{10}$-aminophenyl}carbonyl-3-$R^8$-4-$R^7$-5-$R^6$-6-$R^5$-benzoic acids having the formula

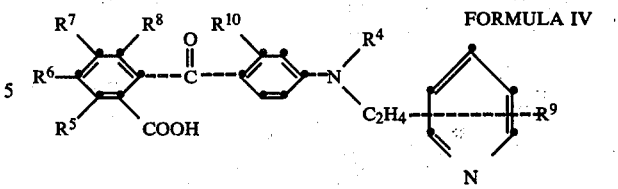

FORMULA IV wherein: $R^4$ represents hydrogen, non-tertiary $C_1$ to $C_4$ alkyl, benzyl or benzyl substituted in the benzene ring by one or two of halo, non-tertiary $C_1$ to $C_4$ alkyl, non-tertiary $C_1$ to $C_4$ alkoxy or nitro; $R^5$,$R^6$,$R^7$ and $R^8$ each independently represent hydrogen, halo, nitro or when $R^5$, $R^8$ and one of $R^6$ and $R^7$ are each hydrogen, the other of $R^6$ and $R^7$ represents nitro or COOH; $R^9$ represents hydrogen, or non-tertiary $C_1$ to $C_4$ alkyl; and $R^{10}$ represents hydroxy or $C_1$ to $C_3$ alkoxy.

In a third composition of matter aspect, the invention resides in the novel anilines which are particularly useful as intermediates to the novel benzoic acids of Formula IV and which are N-$R^4$-N-[2-($R^9$-pyridyl)ethyl]-3-$R^{10}$-anilines having the formula

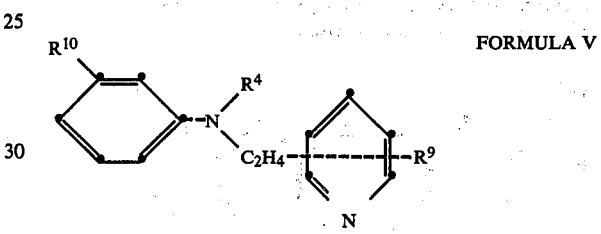

FORMULA V wherein: $R^4$ represents hydrogen, non-tertiary $C_1$ to $C_4$ alkyl, benzyl or benzyl substituted in the benzene ring by one or two of halo, non-tertiary $C_1$ to $C_4$ alkyl, non-tertiary $C_1$ to $C_4$ alkoxy or nitro; $R^9$ represents hydrogen, or non-tertiary $C_1$ to $C_4$ alkyl; and $R^{10}$ represents hydroxy or $C_1$ to $C_3$ alkoxy.

In a fourth composition of matter aspect, the invention resides in the novel anilines which are particularly useful as intermediates to the novel fluorans of Formula I and which are N-$R^1$-N-[2-($R^9$-pyridyl)ethyl]-2-$R^2$-4-$R^{11}$-anilines having the formula

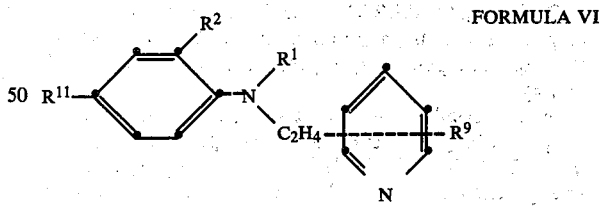

FORMULA VI wherein: $R^1$ represents hydrogen, non-tertiary $C_1$ to $C_8$ alkyl, $C_4$ to $C_8$ cycloalkyl, phenyl, phenyl substituted by one or two of $C_1$ to $C_3$ alkyl, non-tertiary $C_1$ to $C_4$ alkoxy or nitro, benzyl or benzyl substituted in the benzene ring by one or two of halo, non-tertiary $C_1$ to $C_4$ alkyl, non-tertiary $C_1$ to $C_4$ alkoxy or nitro; $R^2$ represents hydrogen, $C_1$ to $C_4$ alkyl or halo; $R^9$ represents hydrogen, or non-tertiary $C_1$ to $C_4$ alkyl; and $R^{11}$ represents hydroxy or $C_1$ to $C_3$ alkoxy.

In one of its process aspects, the invention sought to be patented resides in the process for preparing a 2-(N-R-N-$R^1$)amino-3-$R^2$-6-(N-$R^3$-N-$R^4$)amino-4'-$R^5$-5'-$R^6$-6'-$R^7$-7'-$R^8$-fluoran according to Formula I which comprises interacting in the first step a 2-[2-$R^{10}$-4-(N-$R^3$-N-$R^4$)aminophenyl]carbonyl-3-$R^8$-4-$R^7$-5-$R^6$-6-$R^5$-benzoic acid having the formula

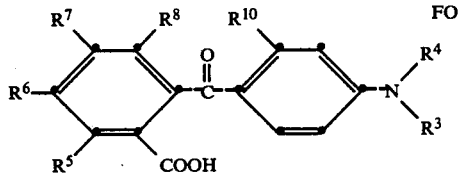

FORMULA VII with a N-R-N-$R^1$-2-$R^2$-4-$R^{11}$-aniline having the formula

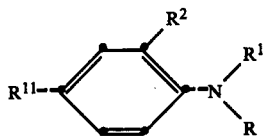

FORMULA VIII in the presence of an acidic condensing agent to obtain a 3-[2-$R^{10}$-4-(N-$R^3$-N-$R^4$)aminophenyl]-3-[2-$R^{11}$-4-$R^2$-5-(N-R-N-$R^1$)aminophenyl]-4-$R^8$-5-$R^7$-6-$R^6$-7-$R^5$-phthalide having the formula

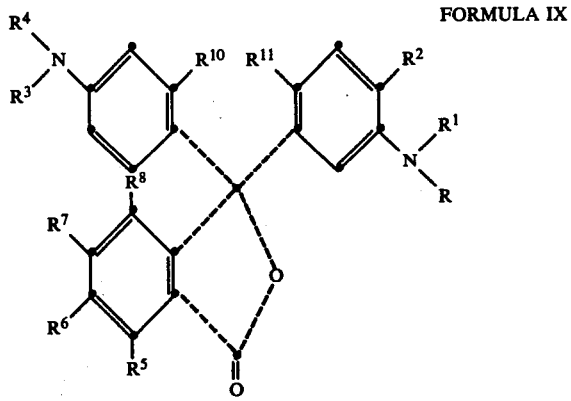

FORMULA IX which, in turn, in a second step is cyclized by heating in the presence of an alkaline substance to obtain the corresponding fluoran of Formula I wherein R,$R^1$,$R^2$,$R^3$,$R^4$, $R^5$,$R^6$,$R^7$ and $R^8$ each have the same respective meanings given in Formula I and $R^{10}$ and $R^{11}$ each independently represent hydroxy or $C_1$ to $C_3$ alkoxy.

In a second of its process aspects, the invention sought to be patented resides in the process for preparing a 2-{2-($R^{10}$-4-N-[2-($R^9$-pyridyl)ethyl]-N-$R^4$-aminophenyl}carbonyl-3-$R^8$-4-$R^7$-5-$R^6$-$R^5$-benzoic acid according to Formula IV which comprises interacting a N-[2-($R^9$-pyridyl)ethyl]-N-$R^4$-3-$R^{10}$-aniline of Formula V with a 3-$R^5$-4-$R^6$-5-$R^7$-6-$R^8$-phthalic anhydride wherein $R^4$,$R^5$,$R^6$,$R^7$,$R^8$,$R^9$ and $R^{10}$each have the same respective meanings given in Formula IV.

In a third of its process aspects, the invention sought to be patented resides in the process for preparing a N-[2-($R^9$-pyridyl)ethyl]-N-$R^1$-4-$R^{11}$-2-$R^2$-aniline according to Formula VI which comprises interacting a N-$R^1$-4-$R^{11}$-2-$R^2$-aniline with a $R^9$-vinylpyridine wherein $R^2$,$R^9$ and $R^{11}$ each have the same respective meanings given in Formula VI.

In a fourth of its process aspects, the invention sought to be patented resides in the process for preparing a N-[2-($R^9$-pyridyl)ethyl]-N-$R^4$-3-$R^{10}$-aniline according to Formula V which comprises interacting a 3-N-$R^4$-$R^{10}$-aniline with a $R^9$-vinylpyridine wherein $R^4$, $R^9$, and $R^{10}$ each have the same respective meanings given in Formula V.

In another of its process aspects, the invention sought to be patented resides in the process for preparing 2-(N-R-N-$R^1$)amino-3-$R^2$-6-(N-$R^3$-N-$R^4$)amino-4'-$R^5$-5'-$R^6$-6'-$R^7$-7'-$R^8$-fluoran according to Formula I, wherein $R^1$ represents formyl, non-tertiary $C_2$ to $C_4$ acyl, benzoyl, benzoyl substituted in the benzene ring by one or two of halo, non-tertiary $C_1$ to $C_4$ alkyl, non-tertiary $C_1$ to $C_4$ alkoxy or nitro, phenylsulfonyl, or phenylsulfonyl substituted in the benzene ring by one or two of halo, non-tertiary $C_1$ to $C_4$ alkyl, non-tertiary $C_1$ to $C_4$ alkoxy or nitro and R,$R^2$,$R^3$,$R^4$,$R^5$,$R^6$,$R^7$ and $R^8$ each have the same respective meanings given in Formula I, which comprises interacting the corresponding 2-(N-R-N-H)amino-3-$R^2$-6-(N-$R^3$-N-$R^4$)amino-4'-$R^5$-5'-$R^6$-6'-$R^7$-7'-$R^8$-fluoran with an appropriate formylating, acylating, benzoylating, or sulfonylating agent selected from the group consisting of formic acid and acetic anhydride, acetic anhydride, propionyl chloride, butyryl chloride, unsubstituted and substituted benzoyl chlorides and unsubstituted and substituted phenylsulfonyl chlorides.

In still another of its process aspects, the invention sought to be patented resides in the process for preparing 2-(N-R-N-$R^1$)amino-3-$R^2$-6-(N-$R^3$-N-$R^4$)amino-5'/6'-COOY-fluorans according to Formula I where in Y represents non-tertiary $C_1$ to $C_{18}$ alkyl and R,$R^1$,$R^2$,$R^3$, and $R^4$ have the same respective meanings given in Formula I, which comprises esterifying the corresponding 2-(N-R-N-$R^1$)amino-3-$R^2$-6-(N-$R^3$-N-$R^4$)amino-5'/6'-carboxy fluoran with an appropriate compound selected from the group consisting of dimethylsulfate, diethylsulfate or Y-halogen in which Y is non-tertiary $C_1$ to $C_{18}$ alkyl in the presence of an alkali metal hydroxide or carbonate.

In yet another of its process aspects, the invention sought to be patented resides in the process for preparing 2-(N-R-N-$R^1$)amino-3-$R^2$-6-(N-$R^3$-N-$R^4$)amino-4'-$R^5$-5-$R^6$-6'-$R^7$-7'-$R^8$-fluorans according to Formula I wherein $R^1$ represents phenylcarbamyl or naphthylcarbamyl and R,$R^2$,$R^3$, $R^4$,$R^5$,$R^6$,$R^7$ and $R^8$ each have the same respective meanings given in Formula I which comprises interacting the corresponding 2-(N-R-N-H)amino-3-$R^2$-6-(N-$R^3$-N-$R^4$)amino-4'-$R^5$-5'-$R^6$-6'-$R^7$-7'-$R^8$-fluoran with an appropriate compound selected from the group consisting of phenylisocyanate and naphthylisocyanate in the presence of an organic base.

In an article of manufacture aspect, the invention sought to be patented resides in a pressure-sensitive carbonless duplicating system or thermal-responsive marking system comprising a support sheet coated with a layer containing as a color-forming substance a 2-(N-R-N-$R^1$)amino-3-$R^2$-6-(N-$R^3$-N-$R^4$)amino-4'-$R^5$-5'-$R^6$-6'-$R^7$-7'-$R^8$-fluoran according to Formula I wherein R,$R^1$,$R^2$,$R^3$,$R^4$,$R^5$, $R^6$,$R^7$ and $R^8$ each have the same respective meanings given in Formula I.

In a particular embodiment in accordance with its article of manufacture aspect, the invention sought to be patented resides in a pressure-sensitive carbonless duplicating system or a thermal-responsive marking system comprising a support sheet coated with a layer containing as a color forming substance a 2-{N-[2-($R^9$-pyridyl)ethyl]-N-$R^1$}amino-3-$R^2$-6-(N-$R^3$-N-$R^4$)amino-4'-$R^5$-

5'-$R^6$-6'-$R^7$-7'-$R^8$-fluoran according to Formula II wherein $R^1,R^2,R^3,R^4,R^5, R^6,R^7,R^8$ and $R^9$ each have the same respective meanings given in Formula I.

Another embodiment in accordance with its article of manufacture aspect, resides in a pressure-sensitive carbonless duplicating system or thermal-responsive marking system comprising a support sheet coated with a layer containing as a color-forming substance a 2-(N-R-N-$R^1$)amino-3-$R^2$-6-{N-[2-($R^9$-pyridyl)ethyl]-N-$R^4$}amino-4'-$R^5$-5'-$R^6$-6'-$R^7$-7'-$R^8$-fluoran according to Formula III wherein R,$R^1$, $R^2,R^4,R^5,R^6,R^7,R^8$ and $R^9$ each have the same respective meanings given in Formula III.

Yet another embodiment in accordance with its article of manufacture aspect, resides in a pressure-sensitive transfer sheet, adapted for use with a receiving sheet having an electron-accepting layer, comprising a support sheet coated on one side with a layer of pressure-rupturable microcapsules; said microcapsules containing a liquid solution of a color-forming substance comprising at least one compound having Formula I.

A further embodiment in accordance with its article of manufacture aspect, resides in a heat responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

As used herein the terms "$C_1$ to $C_3$ alkyl", "non-tertiary $C_1$ to $C_4$ alkyl", "$C_1$ to $C_8$ alkyl" and "non-tertiary $C_1$ to $C_{18}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylhexyl, nonyl, 3-ethylheptyl, n-undecyl, n-dodecyl, n-tridecyl, n-octodecyl, 1,3,5-trimethylhexyl, 1,5-dimethyl-4-ethylhexyl, 5-methyl-2-butylhexyl, 2-propylnonyl, 2-butyloctyl, 2-pentanonyl, 1,2-dimethylhexadecyl and the like.

The terms "$C_1$ to $C_3$ alkoxy" and "non-tertiary $C_1$ to $C_4$ alkoxy" include saturated acyclic, straight or branched-chained groups such as methoxy, ethoxy, propoxy, isopropoxy, butoxy, sec-butoxy and isobutoxy.

As used herein the term "$C_4$ to $C_8$ cycloalkyl" denotes saturated monovalent cyclic aliphatic hydrocarbon radicals including cyclobutyl, cyclopentyl, cyclohexyl, cycloheptyl and cyclooctyl and the like.

The compounds of Formula I hereinabove are essentially colorless in the depicted form. When contacted with an acidic medium, for example, silica gel or one of the types ordinarily employed in pressure-sensitive carbonless duplicating systems such as silton clay or phenolic resins, the compounds of Formula I develop green, red and black-colored images. These developed images are very insensitive to light, are of good tinctorial strength, possess excellent xerographic copiability and enhanced solubility in common organic solvents. The compounds are thus highly suitable for use as colorless precursors, that is, color-forming substances in pressure-sensitive carbonless duplicating systems. The darker green and black colors can be used alone as color formers to produce images which are readily copiable, whereas the red colors can be used alone or as toners in admixture with other color formers to produce images of a neutral shade which desirably are readily copiable by xerographic means.

The compounds of this invention may be incorporated in any of the commercially-accepted systems known in the carbonless duplicating art. A typical technique for such applications is as follows. Solutions containing one or more colorless compounds of Formula I optionally in admixture with other color formers, in suitable solvents are microencapsulated by well-known procedures, for example, as described in U.S. Pat. Nos. 3,649,649, 3,429,827 and 4,000,087. The microcapsules are coated on the reverse side of a sheet with the aid of a suitable binder and the coated transfer sheet is then assembled in a manifold with the microcapsule coated side in contact with a receiving sheet coated with an electron-accepting substance, for example, silton clay or a phenolic resin. Application of pressure to the manifold such as that exerted by a stylus, typewriter or other form of writing or printing causes the capsules on the reverse side to rupture. The solution of the color formers released from the ruptured microcapsules flows to the receiving sheet and on contact with the acidic medium thereon forms black to green and red-colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers such as described in U.S. Pat. No. 3,539,375, that is, papers which produce a colored image when contacted with a heated stylus or heated type, for example, bisphenol A, heating of the mixture produces a colored image of varying shades from black to green and red depending on the particular compound of the invention employed. The ability of the compounds of Formula I to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

The best mode contemplated by the inventors of carrying out this invention will now be described so as to enable any person skilled in the art to which it pertains to make and use the same.

In accordance with one of the aforementioned process aspects of this invention the 2-(N-R-N-$R^1$)amino-3-$R^2$-6-(N-$R^3$-N-$R^4$)amino-4'-$R^5$-5'-$R^6$-6'-$R^7$-7'-$R^8$-fluorans of Formula I are obtained by interacting in a first step in approximately equimolecular proportions an appropriate 2-[2-$R^{10}$-4-(N-$R^3$-N-$R^4$)aminophenyl]carbonyl-3-$R^8$-4-$R^7$-5-$R^6$-6-$R^5$-benzoic acid of Formula VII with an appropriate N-R-N-$R^1$-2-$R^2$-4-$R^{11}$-aniline of Formula VIII. The reaction is conveniently carried out in dehydrating solvent, for example, 100 percent sulfuric acid or a mixture of 100 percent sulfuric acid and oleum at a temperature in the approximate range of 0° to 60° C. for a period of time from 18 hours to 100 hours. The 3-[2-$R^{11}$-4-$R^3$-5-(N-R-N-$R^1$)aminophenyl]-3-[2-$R^{10}$-4-(N-$R^3$-N-$R^4$)aminophenyl]-4-$R^8$-5-$R^7$-6-$R^6$-7-$R^5$-phthalides of Formula IX thus obtained are isolated by adding the reaction mixture to ice-water and collecting the solid thus formed by filtration. In a second step, the 2-(N-R-N-$R^1$)amino-3-$R^2$-6-(N-$R^3$-N-$R^4$)amino-4'-$R^5$-5'-$R^6$-6'-$R^7$-7'-$R^8$-fluorans of Formula I can be conveniently obtained by heating the appropriate 3-[2-$R^{11}$-4-$R^3$-5-(N-R-N-$R^1$)aminophenyl]-3-[2-$R^{10}$-4-(N-$R^3$-N-$R^4$)aminophenyl]-4-$R^8$-5-$R^7$-6-$R^6$-7-$R^5$-phthalide in the presence of an alkali metal hydroxide, for example, sodium hydroxide or potassium hydroxide in an aqueous solution optionally in the presence of an organic liquid, for example, toluene, at a temperature in the range of 40° C. to 115° C. for a period of approximately 90 minutes to approximately 100 hours. If there is no organic liquid present the product is filtered, washed and dried. If there is an organic liquid present, the organic layer containing the product is separated from the water layer, washed with fresh water or saturated aqueous sodium chloride solution and the organic layer is concentrated by evaporation or distillation. The product which precipitates from the organic layer is collected by filtration and washed with an organic liquid, for example, hexane or isopropyl alcohol.

Alternatively, the mixture which results from adding of the sulfuric acid reaction mixture to ice-water can be adjusted to a pH of from 8 to 12 with the addition of an alkali metal hydroxide, for example, sodium hydroxide or potassium hydroxide and then treated in a manner similar to that described above for the conversion of the phthalide to the fluoran.

In the instance in which one of $R^6$ or $R^7$ is a carboxylic acid moiety, the pH of the aqueous slurry before isolation of the 2-(N-R-N-$R^1$)amino-3-$R^2$-6-(N-$R^3$-N-$R^4$)amino-5'/6'-carboxyfluoran is adjusted to between 3 and 4 and the product is collected by filtration.

In accordance with another of the process aspects of the invention, the 2-(N-R-N-$R^1$)amino-3-$R^2$-6-(N-$R^3$-N-$R^4$)amino-5'/6'-COOY-fluorans of Formula I in which Y is a non-tertiary $C_1$ to $C_{18}$ alkyl moiety are obtained by interacting 2-(N-R-N-$R^1$)amino-3-$R^2$-6-(N-$R^3$-N-$R^4$)amino-5'/6'-carboxy fluoran with an appropriate alkylating agent, for example, dimethyl sulfate, diethyl sulfate, ethyl iodide, normal butyl bromide, normal hexadecyl bromide, and the like in an inert dilutent, for example, N,N-dimethylformamide in the presence of an alkali metal hydroxide or carbonate, for example, sodium hydroxide, potassium hydroxide, sodium carbonate or potassium carbonate. The reaction is conveniently carried out at a temperature in the range of 30° to 60° C. for approximately one-half to three hours. The 2-(N-R-N-$R^1$)amino-3-$R^2$-6-(N-$R^3$-N-$R^4$)amino-5'/6'-COOY-fluoran thus obtained is isolated by adding an organic liquid, for example, toluene, and water to the reaction mixture, separating the water layer, washing the organic liquid layer with water or saturated aqueous sodium chloride solution and concentrating the organic layer by evaporation or distillation. The product which separates can be collected by filtration. If a greater purity product is desired it can be recrystallized from a suitable organic liquid or dissolved in a dilute acid, for example, dilute acetic acid and reprecipitated by adding a dilute base, for example, ammonium hydroxide. The product which separates is collected by filtration.

In accordance with still another process aspect of the invention, the 2-(N-R-N-$R^1$)amino-3-$R^2$-6-(N-$R^3$-N-$R^4$)amino-4'-$R^5$-5'-$R^6$-6'-$R^7$-7'-$R^8$-fluoran of Formula I in which $R^1$ represents non-tertiary $C_1$ to $C_4$ acyl, substituted or unsubstituted benzoyl, substituted or unsubstituted phenylsulfonyl can be conveniently obtained by interacting a 2-(N-R-N-H)amino-3-$R^2$-6-(N-$R^3$-N-$R^4$)amino-4'-$R^5$-5'-$R^6$-6'-$R^7$-7'-$R^8$-fluoran with an acylating agent or sulfonating agent, for example, acetic anhydride, acetyl chloride, propionyl chloride, butyryl chloride, formic acid and acetic anhydride, benzoyl chloride, anisoyl chloride, bromobenzoyl chloride, phenylsulfonyl chloride, and the like in the presence of an excess of the acylating or sulfonating agent or on inert dilutent. The reaction is conveniently carried out at a temperature in the range of 20° C. to 50° C. for approximately one hour to approximately twenty-four hours. The appropriate 2-(N-R-N-$R^1$)amino-3-$R^2$-6-(N-$R^3$-N-$R^4$)amino-4'-$R^5$-5'-$R^6$-6'-$R^7$-7'-$R^8$-fluorans thus obtained are isolated by adding the reaction mixture to ice-water, adjusting the pH to approximately 8 with the addition of an alkaline material, for example, ammonium hydroxide, and collecting the solid thus formed by filtration.

In accordance with another of the process aspects of this invention, the 2-(N-R-N-$R^1$)amino-3-$R^2$-6-(N-$R^3$-N-$R^4$)amino-4'-$R^5$-5'-$R^6$-6'-$R^7$-7'-$R^8$-fluorans of Formula I in which in $R^1$ represents phenylcarbamyl or naphthylcarbamyl are obtained by interacting a 2-(N-R-N-H)amino-3-$R^2$-6-(N-$R^3$-N-$R^4$)amino-4'-$R^5$-5'-$R^6$-6'-$R^7$-7'-$R^8$-fluoran with an appropriate isocyanate, for example, phenylisocyanate or naphthylisocyanate in an inert dilutent, for example, toluene, in the presence of an organic base, for example, pyridine. The reaction is conveniently carried out at a temperature in the range of 20° C. to 60° C. for approximately twenty-four to approximately forty-eight hours. The product is isolated by concentrating the reaction solution by distilling or evaporating the inert diluent and collecting the solid thus formed by filtration.

In accordance with another of the process aspects of this invention, the 2-{2-$R^{10}$-4-N-[2-($R^9$-pyridyl)ethyl]-N-$R^4$-aminophenyl}carbonyl-3-$R^8$-4-$R^7$-5-$R^6$-6-$R^5$-benzoic acids according to Formula IV can be conveniently obtained by interacting an appropriate N-[2-($R^9$-pyridyl)ethyl]-N-$R^4$-3-$R^{10}$-aniline with an appropriate 3-$R^5$-4-$R^6$-5-$R^7$-6-$R^8$-phthalic anhydride. The reaction is conveniently carried out in an inert diluent, for example, chlorobenzene at a temperature in the range of 70° C. to the reflux temperature of the inert diluent for a period of time from approximately six hours to approximately twenty-four hours. The product is isolated by evaporating the inert diluent, dissolving the product in a dilute aqueous solution of an alkali metal hydroxide, for example, sodium hydroxide or potassium hydroxide, and extracting the aqueous solution of product with a water immiscible organic liquid, for example, chloroform. The aqueous solution is adjusted to a pH in the range of 3.4 to 7.2 using a dilute mineral acid, for example, hydrochloric acid, and the product is collected by filtration.

In accordance with one of the process aspects of this invention, the N-[2-($R^9$-pyridyl)ethyl]-N-$R^4$-3-$R^{10}$-anilines of Formula V are obtained by interacting an appropriate N-$R^4$-3-$R^{10}$-aniline with an appropriate $R^9$-vinylpyridine. The reaction is conveniently carried out in a mixture of an aliphatic organic acid and an aliphatic alcohol, for example a mixture of acetic acid and methyl alcohol at a temperature in the range of 45° C. to 80° C. for approximately 2 to approximately eight hours. The product is isolated by dissolving the product in an organic liquid, for example, dichoromethane, washing the organic liquid layer with water, and concentrating the organic layer by evaporating the liquid. The product is collected by filtation.

In accordance with another process aspect of the invention, the N-[2-($R^9$-pyridyl)ethyl]-N-$R^1$-4-$R^{11}$-2-$R^2$-anilines according to Formula VI are obtained by interacting an appropriate N-$R^1$-4-$R^{11}$-2-$R^2$-aniline with an appropriate $R^9$-vinylpyridine. The reaction is conveniently carried out in a mixture of an aliphatic organic acid and an aliphatic alcohol, for example, acetic acid and methyl alcohol at a temperature in the range of 60° C. to the reflux temperature of the organic acid for a period of time from approximately six hours to approximately twenty-four hours. The product is isolated by adding the reaction mixture into an aqueous solution containing an alkali metal bicarbonate, for example, sodium bicarbonate or potassium bicarbonate and a water immiscible organic liquid, for example, toluene. The organic layer containing the product is separated, wash with aqueous sodium chloride solution and the organic liquid is removed by evaporation. The resulting product may be purified by conventional means, for example, recrystallization or column chromatography.

The 2-[2-$R^{10}$-4-(N-$R^3$-N-$R^4$)aminophenyl]carbonyl-4/5-carboxybenzoic acids according to Formula VII required for the preparation of 2-(N-R-N-$R^1$)amino-3-$R^2$-6-(N-$R^3$-N-$R^4$)amino-5'/6'carboxyfluorans according to Formula I are generally known or if specifically new can be prepared in accordance with the procedures described hereinabove.

It will, of course, be appreciated that the reaction of trimellitic anhydride with a N-$R^3$-N-$R^4$-3-$R^{10}$-aniline can produce isomers or mixtures of isomers viz. 2-[2-$R^{10}$-4-(N-$R^3$-N-$R^4$)aminophenyl]carbonyl-4-carboxy benzoic acids and 2-[$R^{10}$-4-(N-$R^3$-N-$R^4$)amino-phenyl]-carbonyl-5-carboxybenzoic acids. In the latter instance, the isomeric mixtures of benzoic acids can be separated by conventional means such as fractional crystallization or chromatography. Alternatively, the isomeric mixtures of the 4/5-carboxybenzoic acids can be reacted with the appropriate N-R-N-$R^1$-2-$R^2$-4-$R^{11}$-aniline to produce a mixture of 5- and 6-carboxyphthalides of Formula IX which, if desired, can be separated or simply used as a mixture in preparing the final products of Formula I. Throughout this application where the possibility of different isomeric products being formed is present, the nomenclature 4/5, 5/6 and 5'/6' is adopted, meaning the product obtained or claimed is a mixture of the isomers.

The N-$R^4$-3-$R^{10}$-anilines, the N-R-N-$R^1$-2-$R^2$-4-$R^{11}$-anilines, the 3-$R^5$-4-$R^6$-5-$R^7$-6-$R^8$-phthalic anhydrides, the $R^9$-vinylpyridines and the 2-[2-$R^{10}$-4-(N-$R^3$-N-$R^4$)aminophenyl]carbonyl-3-$R^8$-4-$R^7$-5-$R^6$-6-$R^5$-benzoic acids of Formula VII in which $R^3$ is other than 2-($R^9$-pyridyl)ethyl required as starting materials in the processes of this invention belong to well known chemical classes of compounds and are either commercially available or readily obtained by conventional procedures well known in the art.

The molecular structures of the compounds were assigned on the basis of the modes of synthesis and a study of their infrared, nuclear magnetic resonance, and mass spectra.

The following examples will further illustrate the invention, without, however, limiting it thereto.

EXAMPLE 1

A. With stirring a mixture of 20.0 g (0.16 mole) of 4-anisidine, 25.2 g (0.24 mole) of 2-vinylpyridine, 1.8 ml of glacial acetic acid and 50.0 ml of anhydrous methyl alcohol was maintained at reflux temperature for approximately twenty hours. The reaction mixture was cooled to room temperature and slowly added to a mixture of aqueous sodium bicarbonate solution and toluene. The aqueous layer was separated saving the organic layer and the aqueous layer was extracted a second time with toluene. The two toluene layers were combined and washed with an aqueous saturated sodium chloride solution. After drying over anhydrous sodium sulfate, the organic layer was evaporated under reduced pressure to obtain 41.9 g of an oil. Five grams of the oil was purified by column chromatography passing it through approximately 100 g of 40–140 mesh silica gel using ethyl acetate as the carrier to obtain 3.2 g of N-[2-(2-pyridyl)ethyl]-4-methoxy-aniline (Formula VI:$R^1=R^2=R^9=H$; $R^{11}=CH_3O$), a pale tan solid which melted at 51°–53° C. The infrared spectrum had significant maxima at 1595 cm$^{-1}$ (C=C;m) and 1238 cm$^{-1}$ (C-O;s). The nuclear magnetic resonance spectrum was in accord with the assigned structure. The remaining 36.9 g of oil was distilled at 0.8 mm Hg collecting the fraction which boiled over the range 185°–191° C.

B. With stirring 14.8 g (0.044 mole) of 2-(2-hydroxy-4-diethylaminophenyl)carbonyl benzoic acid was added slowly to 60.0 ml of 100 percent sulfuric acid previously warmed to a temperature in the range of 35° to 40° C. After all the solid had dissolved, the resulting solution was cooled to approximately 30° C. and 10.0 g (0.044 mole) of N-2-[(2-pyridyl)ethyl]-4-methoxyaniline was added in small portions while maintaining approximately 30° C. using an external cold water bath to cool the reaction mixture. The reaction mixture was stirred overnight at ambient temperature. With stirring the mixture was added slowly to ice and the pH of the resulting mixture was adjusted to approximately 10 with the addition of 50 percent aqueous sodium hydroxide. The resulting mixture was heated to approximately 75° C. and toluene was added. This mixture was maintained at approximately 85° C. for approximately two days. After cooling to room temperature, the aqueous layer was separated from the toluene layer and the water layer was extracted with a second portion of toluene. The two toluene layers were combined, washed twice with saturated aqueous sodium chloride solution and dried over anhydrous sodium sulfate. The dried toluene solution was evaporated under reduced pressure resulting in a red tar which was triturated with with hexane to obtain 11.5 g of 2-[2-(2-pyridyl)ethyl)-]amino-6-diethyl-aminofluoran (Formula II: $R^1=R^2=R^5=R^6=R^7=R^8=R^9=H;R^3=R^4=C_2H_5$), a pale purple colored solid. The solid was dissolved in a 1:1 (V:V) mixture of isopropyl alcohol and hexane and treated hot with decolorizing carbon. The mixture was filtered to remove the carbon, cooled, and the solid collected by the filtration and dried to obtain 7.5 g of a pale beige-colored solid which melted at 139°–142° C. A significant infrared maximum appeared at 1760 cm$^{-1}$ (C=O;s). The nuclear magnetic resonance spectrum was consistent with the assigned structure. A toluene solution of the product spotted on an acidic clay-coated paper and on a phenolic resin-coated paper developed a green-colored image.

C. With stirring a mixture of 10.0 g (0.02 mole) of 2-[2-(2-pyridyl)ethyl]amino-6-diethylaminofluoran, 50.0 ml of isopropyl alcohol 6.9 g of potassium carbonate and 5.02 g (0.04 mole) of benzyl chloride was heated at reflux overnight. In the morning an additional 4.84 g (0.038 mole) of benzyl chloride was added to the mixture and reflux was maintained for approximately twenty-four hours. Slowly, water was added to the reaction mixture and the resultant mixture was heated at reflux temperature for approximately two hours. The mixture was extracted twice with toluene and the two toluene layers were combined. The toluene was removed by distillation leaving a tar-like residue. The tar-like product was purified by passing it through a silica gel packed chromatography column using ethyl acetate:toluene (V:V) as the eluent to obtain 3.4 g of 2-{N-benzyl-N-[2-(2-pyridyl)ethyl]amino}-6-diethylaminofluoran (Formula II: $R^1=C_6H_5CH_2$; $R^2=R^5=R^6=R^7=R^8=R^9=H$; $R^3=R^4=C_2H_5$), a white solid which melted at 108°–112° C. A significant infrared maximum appeared at 1745 cm$^{-1}$ (C=O;s). The nuclear magnetic resonance spectrum was in accord with the assigned structure. A toluene solution of the product spotted on an acidic clay-coated paper or a phenolic resin-coated paper developed a green-colored image.

EXAMPLE 2

A. A mixture of 50.0 g (0.4 mole) of 2-methyl-4-hydroxyaniline, 2.4 g of glacial acetic acid and 125.0 ml of anhydrous methyl alcohol was heated to reflux with stirring and 63.1 g (0.6 mole) of 2-vinylpyridine was added dropwise to the mixture. The resultant reaction mixture was maintained at reflux for approximately forty-eight hours, cooled to ambient temperature and added to a mixture of aqueous sodium bicarbonate and toluene. The water layer was separated from to toluene layer and the water layer was extracted a second time with toluene. The two toluene layers were combined, washed with saturated aqueous sodium chloride solution and dried over anhydrous sodium sulfate. The solid, which crystallized from the toluene upon standing, was collected by filtration, washed with hexane and dried to obtain 23.6 g of N-[2-(2-pyridyl)ethyl]-2-methyl-4-hydroxyaniline (Formula VI: $R^1=R^9=H$; $R^2=CH_3$; $R^{11}=OH$), a pale beige-colored solid which melted at 137.5°–139.5° C. after recrystallization from toluene. Significant infrared maxima appeared at 3200 cm$^{-1}$ (OH;m) and 1601 cm$^{-1}$ (C=C;m). The nuclear magnetic resonance spectrum was in accord with the assigned structure.

B. With stirring 14.8 g (0.044 mole) of 2-(2-hydroxy-4-diethylaminophenyl)carbonylbenzoic acid was added slowly to 60.0 ml of 100 percent sulfuric acid which had been heated to approximately 40° C. After all the solid dissolved, the resulting solution was cooled to room temperature and 10.0 g (0.044 mole) of N-[2-(2-pyridyl)ethyl]-2-methyl-4-hydroxyaniline, prepared in part A above, was added slowly maintaining a temperature under 40° C. The reaction mixture was stirred overnight at ambient temperature. In the morning the reaction mixture was poured slowly onto ice with stirring and to the resulting mixture 50 percent aqueous sodium hydroxide was added slowly to adjust the pH to approximately 11 while maintaining a temperature under 40° C. by gradually adding ice to the reaction mixture. The resulting mixture was maintained at a temperature in the range of 40°–45° C. for approximately one hour after which time the mixture was cooled to room temperature and the pH adjusted to approximately 7.5 with the gradual addition of dilute sulfuric acid. The solid present in the mixture was collected by filtration, washed with water and dried in vacuo to obtain 12.0 g of 2-[2-(2-pyridyl)ethyl]amino-3-methyl-6-diethylaminofluoran (Formula II: $R^1=R^5=R^6=R^7=R^8=R^9=H$; $R^2=CH_3$; $R^3=R^4=C_2H_5$), a pale green-colored solid which melted at 85°–90° C. A significant infrared maximum appeared at 1755 cm$^{-1}$ (C=O;s). The nuclear magnetic resonance spectrum was consistent with the assigned structure. A toluene solution of the product spotted on an acidic clay-coated paper developed a grey-colored image and on a phenolic resin-coated paper developed a green-colored image.

EXAMPLE 3

A. A mixture of 50.0 g (0.4 mole) of 2-methyl-4-hydroxyaniline, 2.4 g of glacial acetic acid and 125.0 ml of anhydrous methyl alcohol was heated to reflux with stirring and 63.1 g (0.6 mole) of 4-vinylpyridine was added dropwise. The resulting reaction mixture was refluxed approximately seventy-two hours. After cooling the reaction mixture to ambient temperature, the solid was collected by filtration, washed twice with fresh methanol, and dried in vacuo to obtain 30.9 g of N-2-[2-(4-pyridyl)ethyl]-2-methyl-4-hydroxyaniline (Formula VI: $R^1=R^9=H$; $R^2=CH_3$; $R^{11}=OH$), a colored solid which melted at 146°–148.5° C. A significant infrared maximum appeared at 3410 cm$^{-1}$ (OH;m). The nuclear magnetic resonance spectrum was in accord with the assigned structure.

B. At approximately 40° C., 14.8 g (0.044 mole) of 2-(2-hydroxy-4-diethylaminophenyl)carbonylbenzoic acid was added to 60.0 ml of 100 percent sulfuric acid with stirring. When all of the solid was dissolved, the solution was cooled to approximately 30° C. and 10.0 g (0.044 mole) of N-[2-(4-pyridyl)ethyl]-2-methyl-4-hydroxy-aniline, prepared in part A above, was added in small portions while maintaining a temperature of approximately 30° C. by means of an external ice-water bath. The resulting reaction mixture was stirred approximately eighteen hours at ambient temperature and then slowly poured onto ice with stirring. The resulting slurry was adjusted to pH 10 to 11 with the addition of 50 percent aqueous sodium hydroxide. The blue-grey-colored solid was collected by filtration, reslurried in fresh water, filtered and dried to obtain 2-[2-(4-pyridyl)ethyl]amino-3-methyl-6-diethylaminofluoran (Formula II: $R^1=R^5=R^6=R^7=R^8=R^9=H$; $R^2=CH_3$; $R^3=R^4=C_2H_5$), a grey-colored solid. A significant infrared maximum appeared at 1750 cm$^{-1}$ (C=O;s). The nuclear magnetic resonance spectrum was concordant with the assigned structure. A toluene solution of the product spotted on an acidic clay-coated paper and on a phenolic resin-coated paper developed a green colored image.

EXAMPLE 4

With stirring 1.0 g (0.002 mole) of 2-[2-(2-pyridyl)ethyl]amino-6-diethylaminofluoran, prepared in a manner similar to Example 1, part B above, was added to 5.0 ml of 90 percent aqueous formic acid; and when the solution was complete 1.6 ml of acetic anhydride was added. The resulting solution was stirred at ambient temperature for approximately one hour and poured onto a mixture of ice and water. The resulting slurry was adjusted to a pH of approximately 7 with the addition of concentrated ammonium hydroxide. The solid was collected by filtration, washed with water and dried to obtain 1.1 g of 2-{N-[2-(2-pyridyl)ethyl]-N-formyl}amino-6-diethylaminofluoran (Formula II: $R^1$=CHO; $R^2$=$R^5$=$R^6$=$R^7$=$R$=$^8$=$R^9$=H; $R^3$=$R^4$=$C_2H_5$), a beige-colored solid which melted at 85°–90° C. The infrared spectrum had a significant maximum at 1761 cm$^{-1}$ (C=O;s). The nuclear magnetic resonance spectrum was in accord with the assigned structure. A toluene solution of the product spotted on an acidic clay-coated paper and on a phenolic resin-coated paper developed an orange-red-colored image.

EXAMPLE 5

Proceeding in a manner similar to that described above in Example 4, 3.0 g (0.061 mole) of 2-[2-(2-pyridyl)ethyl]amino-6-diethylaminofluoran, prepared in a manner similar to Example 1, part B above, and 20.0 ml of acetic anhydride were interacted to obtain 2.4 g of 2-{N-2-[2-(2-pyridyl)ethyl]-N-(acetyl)}amino-6-diethylaminofluoran (Formula II: $R^1$=CH$_3$CO; $R^2$=$R^5$=$R^6$=$R^7$=$R^8$=$R^9$=H; $R^3$=$R^4$=$C_2H_5$), a pale pink-colored solid which melted at 90°–95° C. A significant infrared maximum appeared at 1757 cm$^{-1}$ (C=O;s). The nuclear magnetic resonance spectrum was consistent with the assigned structure. A toluene solution of the produce spotted on an acidic clay-coated paper and on a phenolic resin-coated paper developed on orange-red colored image.

EXAMPLE 6

With stirring 1.0 g (0.002 mole) of 2-[2-(2-pyridyl)ethyl]amino-6-diethylaminofluoran, prepared in a manner similar to the one described in Example 1, part B above, was added to 20.0 ml of toluene. To this slurry there was added 2 drops of pyridine and 0.34 g (0.002 mole) of 1-naphthyl isocyanate and the resulting reaction mixture was stirred approximately twenty-four hours at ambient temperature. The solution was concentrated at reduced pressure to obtain 1.2 g of 2-{N-[2-(2-pyridyl)ethyl]-N-(napthylcarbamyl)}amino-6-diethylamino-fluoran (Formula II: $R^1$=naphthyl-NHCO: $R^2$=$R^5$=$R^6$=$R^7$=$R^8$=$R^9$=H; $R^3$=$R^4$=$C_2H_5$), a pale pink-colored solid which melted at 77°–83° C. A significant infrared maxima appeared at 1761 cm$^{-1}$ (C=O;s). The nuclear magnetic resonance spectrum was in accord with the assigned structure. A toluene solution of the product spotted on an acidic clay-coated paper and on a phenolic resin-coated paper developed a red-colored image.

EXAMPLE 7

Proceeding in a manner similar to that described in Example 6 above, 2.0 g (0.004 mole) of 2-[2-(2-pyridyl)ethyl]amino-3-methyl-6-diethylaminofluoran, 10.0 ml of 90 percent aqueous formic acid and 3.2 ml of acetic anhydride were interacted to obtain 1.9 g of 2-{(N-formyl)-N-[2-(pyridyl)ethyl]}amino-3-methyl-6-diethylaminofluoran (Formula II: $R^1$=CHO; $R^2$=CH$_3$; $R^3$=$R^4$=$C_2H_5$; $R^5$=$R^6$=$R^7$=$R^8$=$R^9$=H;) a beige-colored solid which melted over the range of 100°–110° C. A significant infrared maximum appeared at 1752 cm$^{-1}$ (C=O;s). The nuclear magnetic resonance spectrum was in accord with the assigned structure. A toluene solution of the product spotted on an acidic clay-coated paper and on a phenolic resin-coated paper developed an orange-red-colored image.

EXAMPLE 8

Following the procedure described in Example 6 above, 1.0 g (0.002 mole) of 2-[2-(2-pyridyl)ethyl]amino-3-methyl-6-diethylaminofluoran and 10.0 ml of acetic anhydride were interacted to obtain 0.75 g of 2-{(N-acetyl)-N-[2-(2-pyridyl)ethyl]}amino-3-methyl-6-diethylaminofluoran (Formula II: $R^1$=CH$_3$CO; $R^2$=CH$_3$; $R^3$=$R^4$=$C_2H_5$; $R^5$=$R^6$=$R^7$=$R^8$=$R^9$=H), a tan-colored solid which melted at 97°–101° C. The infrared spectrum had a significant maximum at 1755 cm$^{-1}$ (C=O;s). The nuclear magnetic resonance spectrum was consistent with the assigned structure. A toluene solution of the product spotted on on an acid clay-coated paper and on a phenolic resin-coated paper developed an orange-red-colored image.

EXAMPLE 9

In a manner similar to that described in Example 6 above, 2.0 g (0.004 mole) of 2-[2-(2-pyridyl)ethyl]amino-3-methyl-6-diethylaminofluoran and 0.68 g (0.004 mole) of 1-naphthyl isocyanate were interacted in 15.0 ml of toluene in the presence of 4 drops of pyridine to obtain 1.8 g of 2-{N-(1-naphthylcarbamyl-N-[2-(2-pyridyl)ethyl]}amino-3-methyl-6-diethylaminofluoran (Formula II: $R^1$=naphthyl-NHCO; $R^2$=CH$_3$; $R^3$=$R^4$=$C_2H_5$; $R^5$=$R^6$=$R^7$=$R^8$=$R^9$=H), beige-colored solid that melted at 102°–105° C. A significant infrared maximum appeared at 1762 cm$^{-1}$ (C=O;s). The nuclear magnetic resonance spectrum was in accord with the assigned structure. A toluene solution of the product spotted on an acidic clay-coated paper and on a phenolic resin-coated paper developed an orange-red-colored image.

EXAMPLE 10

A. With stirring 10.6 g (0.044 mole) of N-[2-(2-pyridyl)ethyl]-4-methoxy-aniline, prepared in a manner similar to that described in Example 1, part A, was added to 25.0 ml of dimethylsulfoxide. After the solution was complete, 4.9 g of ground potassium hydroxide was added slowly to the solution maintaining a temperature under 40° C. After approximately one hour 13.6 g (0.088 mole) of diethylsulfate was added dropwise to the reaction mixture while maintaining a temperature in the range of 25°–40° C., and the resultant mixture was stirred for approximately eighteen hours at ambient temperature. To the reaction mixture there was added 50.0 ml of toluene with stirring. The insoluble potassium sulfate was collected by filtration and discarded. The toluene solution was washed several times with saturated aqueous sodium chloride solution and dried with anhydrous sodium sulfate. The toluene was removed under reduced pressure to obtain 5.5 g of N-ethyl-N-[2-(2-pyridyl)ethyl]-4-methoxyaniline (Formula VI: $R^1$=$C_2H_5$; $R^2$=$R^9$=H; $R^{11}$=CH$_3$O) a brown-colored oil. A significant infrared maximum appeared at 1592 cm$^{-1}$ (C=C;s). The nuclear magnetic resonance spectrum was consistent with the assigned structure.

B. Slowly, 6.3 g (0.02 mole) of 2-(2-hydroxy-4-diethylaminophenyl)carbonylbenzoic acid was added to 30.0 ml of 100 percent sulfuric acid with stirring. The resulting solution was cooled to approximately 25° C. and 5.0 g (0.02 mole) of N-ethyl-N-[2-(2-pyridyl)ethyl]-4-methoxy-aniline was added drop-wise while maintaining a temperature in the range of 25°–30° C. utilizing an ice-water bath. The reaction mixture was stirred approximately eighteen hours at ambient temperature, and approximately fifty-six hours at approximately 45° C. and then cooled to ambient temperature. The resultant solution was poured gradually onto ice with stirring and the resulting slurry was adjusted to approximately pH 5 with the addition of 50 percent aqueous sodium hydroxide. The solid was collected by filtration, reslurried in water and filtered. Then the solid was suspended in a mixture of dilute sodium hydroxide and toluene and maintained at reflux for approximately two days. After cooling, the water layer was separated and extracted with a second portion of toluene. The two toluene layers were combined, dried over anhydrous sodium sulfate and the toluene was removed by distillation. The residue was triturated with hexane but no solid was formed. The hexane was evaporated and the resulting tar-like solid was dissolved in acetone. The resulting solution was added dropwise into water containing several milliliters of concentrated ammonium hydroxide. The solid which formed was collected by filtration, washed with water and dried to obtain 3.3 g of 2-{N-ethyl-N-[2-(2-pyridyl)ethyl]}amino-6-diethylaminofluoran (Formula II: $R^1=R^3=R^4=C_2H_5$; $R^2=R^5=R^6=R^7=R^8=R^9=H$), a red-colored solid which melted over the range 60°–70° C. A significant infrared maximum appeared at 1758 cm$^{-1}$ (C=O;s). The nuclear magnetic resonance spectrum was in accord with the assigned structure. A toluene solution of the product spotted on an acidic clay-coated paper and on a phenolic resin-coated paper developed a green-colored image.

EXAMPLE 11

A. A mixture of 14.8 g (0.1 mole) of phthalic anhydride, 16.3 g (0.1 mole) of 100 percent 3-pyrrolidinophenol and 50.0 ml of 1,2-dichloroethane was maintained at approximately 40° C. for approximately twenty-four hours, at approximately 60° C. for approximately twenty-four hours and at reflux temperature for approximately twelve hours. After cooling the reaction mixture to ambient temperature, the solid which precipitated was collected by filtration and washed with 500.0 ml of 1,2-dichloroethane. The solid was dissolved in dilute aqueous sodium hydroxide, the resulting mixture was filtered to remove insolubles. The filtrate was adjusted to pH 7.0 with the addition of glacial acetic acid and the solid tar-like material which formed was collected by filtration. To the filtrate an additional amount of glacial acetic acid was added. The solid which precipitated was collected by filtration, washed with water and dried to obtain 11.3 g of 2-(2-hydroxy-4-pyrrolidinophenyl)carbonylbenzoic acid, a pale pink-colored solid which melted at 190°–192° C. To the filtrate there was added an additional portion of glacial acetic acid and the solid which was collected by filtration, washed with water and dried to obtain 0.3 g a pale yellow-colored crystals of the desired product which melted at 193°–195° C. The infrared spectra of the two solids were identical having significant maxima at 1100 cm$^{-1}$ (C=O;m). The nuclear magnetic spectra were consistent with the assigned structure.

B. With stirring 5.0 g (0.016 mole) of 2-(2-hydroxy-4-pyrrolidinylphenyl)carbonylbenzoic acid was added slowly to 25.0 ml of 100 percent sulfuric acid keeping the temperature of the reaction mixture below 25° C. by means of a cold water bath. When the solution was complete, 4.0 g (0.018 mole) of N-[2-(2-pyridyl)ethyl]-4-hydroxy-2-methyl-aniline was added gradually maintaining a temperature under 30° C. by means of an ice-water bath. The resulting mixture was stirred at ambient temperature over the week-end. The reaction mixture was poured slowly onto ice with stirring and the resulting slurry was adjusted to pH 12 with the gradual addition of 50 percent aqueous sodium hydroxide and ice. The slurry was heated to approximately 50° C. and maintained at that temperature for approximately ninety minutes and then allowed to cool to ambient temperature with stirring. The pH of the slurry was adjusted 7.0 with the gradual addition of concentrated hydrochloric acid. The solid was collected by filtration, washed with water and dried to obtain 5.8 g of 2-[2-(2-pyridyl)ethyl]amino-3-methyl 6-pyrrolidinofluoran (Formula II: $R^1$-$R^5=R^6=R^7=R^8=R^9=H$; $R^2=CH_3$;

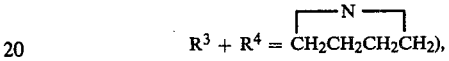
$R^3 + R^4 = CH_2CH_2CH_2CH_2$), a purple-colored solid which melted at 145°–150° C. A significant infrared maximum appeared at 1760 cm$^{-1}$ (C=O;s). The nuclear magnetic resonance spectrum was consistent with the assigned structure.

EXAMPLE 12

To 60.0 ml of 100 percent sulfuric acid there was added with stirring in small portions 15.7 g (0.044 mole) of 2-(2-hydroxy-4-diethylaminophenyl)carbonyl-4/5-carboxybenzoic acid. To the resulting solution there was added gradually 10.0 g (0.044 mole) of N-[2-(2-pyridyl)ethyl]-2-methyl 4-hydroxy-aniline while maintaining a temperature below 35° C. by means of an ice-water bath. After stirring the reaction mixture for approximately thirty-two hours at ambient temperature, the mixture was heated to approximately 35° C. and maintained for approximately twenty hours. The reaction mixture was then maintained at approximately 60° C. for approximately twenty-four hours, cooled to ambient temperature and slowly poured onto ice with stirring. The resulting slurry was adjusted to approximately pH 3.5 using 50 percent aqueous sodium hydroxide and ice. The solid was collected by filtration, the filtercake reslurried in water, filtered and dried to obtain 20.5 g of 2-[2-(2-pyridyl)ethyl]amino-3-methyl-6-diethylamino-5'/6'-carboxyfluoran (Formula II: $R^1=R^5=R^6/R^7=R^8=R^9=H$; $R^2=CH_3$; $R^3=R^4=C_2H_5$; $R^6/R^7=COOH$), a dark green-colored solid which melted over the range 160°–175° C. A significant infrared maximum appeared at 1714 cm$^{-1}$ (C=O;s). The nuclear magnetic resonance spectrum was concordant with the assigned structure.

EXAMPLE 13

With stirring 2.0 g (0.0036 mole) of 2-[2-(2-pyridyl)ethyl]amino-3-methyl-6-diethylamino-5'/6'-carboxyfluoran, from Example 12 above, was added to 10.0 ml of N,N-dimethylformamide and slowly 1.1 g of potassium carbonate was added. To the reaction mixture, 1.1 g (0.004 mole) of diethylsulfate was added and the resulting mixture was stirred overnight. Toluene was added to the resulting mixture. The toluene solution was separated, washed three times, each with 50.0 ml of water and the toluene was removed under reduced pressure to obtain a tar-like solid. The solid was dissolved in dilute acetic acid and the pH was adjusted to approximately 7.5 with the addition of concentrated ammonium hydroxide. The solid which formed was collected by filtration and dried to obtain 0.6 g of 2-[2-(2-pyridyl)ethyl]amino-3-methyl-6-diethyl-amino-5'/6'-ethoxycarbonylfluoran (Formula II: $R^1=R^5=R^6/R^7=R^8=R^9=H$; $R^2=CH_3$; $R^3=R^4=C_2H_5$; $R^6/R^7=COOC_2H_5$), a pale violet-colored solid which melted over the range 75°–85° C. A significant infrared maximum appeared a 1760 cm$^{-1}$ (C=O;s). The nuclear magnetic resonance spectrum was in accord with the assigned structure. A toluene solution of the product spotted on an acidic clay-coated paper or a phenolic resin-coated paper developed a green-colored image.

EXAMPLE 14

Slowly, 15.8 g (0.044 mole) of 2-(2-hydroxy-4-diethylaminophenyl)carbonyl-6-nitrobenzoic acid was added to 60.0 ml of 100 percent sulfuric acid with stirring keeping the temperature under 40° C. with a cold water bath. When the solid was dissolved completely there was added gradually, 10.0 g (0.044 mole) of N-[2-(2-pyridyl)ethyl]-2-methyl-4-hydroxy-aniline keeping the temperature under 25° C. by means of an ice-water bath. The reaction mixture was stirred approximately eighteen hours at ambient temperature and then maintained at approximately 45° C. for approximately six hours and finally maintained a temperature in the range of 155°–160° C. for approximately one hundred and sixty-two hours. After cooling to ambient temperature, the reaction mixture was poured slowly onto ice with stirring. The pH of the resulting slurry was adjusted to approximately 12 by the gradual addition of 50 percent aqueous sodium hydroxide and ice. The slurry was maintained at approximately 50° C. for approximately three hours and allowed to cool to ambient temperature. The pH was adjusted to approximately 7.5 by slowly adding concentrated hydrochloric acid. The mixture was filtered to obtain a black gum-like solid. The solid was dissolved partially in dilute sodium hydroxide solution at approximately pH 11 and the insolubles were collected by filtration. The filtrate was adjusted of pH 8 by adding concentrated hydrochloric acid and the solid which formed was collected by filtration, washed with water and dried to obtain 0.5 g of a black-colored solid. The filtrate was adjusted slowly to pH 5.0 with the addition of concentrated hydrochloric acid. The solid which formed was collected by filtration, washed with water and dried to obtain 2.3 g of dark green-colored solid. It was determined from both infrared and nuclear magnetic resonance spectral analysis that both solids contain isomers of 2-[2-(2-pyridyl)ethyl]amino-3-methyl-6-diethylamino-4'/7'-nitrofluoran. (Formula II: $R^1=R^5/R^8=R^6=R^7=R^9=H$; $R^2=CH_3$; $R^3=R^4=C_2H_5$; $R^5/R^8=NO_2$).

EXAMPLE 15

A mixture of 6.9 g (0.022 mole) of 2-(2-hydroxy-4-diethylaminophenyl)carbonylbenzoic acid and 30.0 ml of 100 percent sulfuric acid was stirred until a complete solution resulted. Slowly, 5.0 g (0.022 mole) of N-[2-(4-pyridyl)ethyl]-4-methoxy-aniline was added to the solution maintaining a temperature under 30° C. during the addition by means of an ice-water bath. The reaction mixture was stirred overnight at ambient temperature and the reaction mixture was heated to approximately 45° C. and maintained for approximately fifty-six hours. After the reaction mixture was cooled to ambient temperature, it was poured slowly onto ice with stirring and the resulting slurry was adjusted to approximately pH 5 by the gradual addition of 50 percent aqueous sodium hydroxide. The solid was collected by filtration, washed with water and dried to obtain 12.5 g of solid. The solid was reslurried in water and sufficient 50 percent aqueous sodium hydroxide was added to adjust the pH to approximately 10. To the resulting slurry 300.0 ml of toluene was added and the mixture was maintained at reflux for approximately sixteen hours. The water layer was separated and extracted with fresh toluene. The two toluene layers were combined and concentrated by distillation to a pot temperature of 114° C. After cooling to room temperature, the pale brown solid, which precipitated from solution, was collected by filtration, washed with hexane and dried to obtain 2.6 g of 2-[2-(4-pyridyl)ethyl]amino-6-diethylaminofluoran (Formula II: $R^1=R^2=R^5=R^6=R^7=R^8=R^9=H$; $R^3=R^4=C_2H_5$), a bright red-colored solid.

EXAMPLE 16

A. A mixture of 23.0 g of glacial acetic acid and 25.9 g (0.2 mole) of 95.2 percent N-methyl-3-hydroxy-aniline was heated to approximately 60° C. and slowly 22.8 g (0.21 mole) of 97 percent 2-vinylpyridine was added at a rate to maintain a temperature in the range of 60°–65° C. After the addition was complete the reaction mixture was maintained at approximately 60° C. for approximately fifteen minutes and then cooled to ambient temperature. Methylene dichloride and approximately 925 ml of water were added slowly to the reaction mixture and the acetic acid was removed in the water layer. After separating the water layer, the organic layer was concentrated at reduced pressure to obtain after washing with water 29.0 g of a viscous brown liquid which analyzed 79.1 percent N-methyl-N-[2-(2-pyridyl)ethyl]-3-hydroxyaniline (Formula V: $R^4=CH_3$; $R^9=H$; $R^{10}=OH$) by gas chromatographic analysis.

B. With stirring, a mixture of 29.0 g of 79.1 percent N-methyl-N-[2-(2-pyridyl)ethyl]-3-hydroxyaniline from part A above, 29.6 g of phthalic anhydride and 120.0 ml of chlorobenzene was maintained at approximately 90° C. for approximately twenty-four hours. After cooling to ambient temperature, the stirring was stopped and a heavy tar-like solid settled out of the reaction mixture. The chlorobenzene was decanted away from the solid and concentrated under reduced pressure. The resulting residue was dried in vacuo over a weekend to obtain 21.9 g of 2-{2-hydroxy-4-N-methyl-N-[2-(2-pyridyl)ethyl]aminophenyl}carbonylbenzoic acid (Formula IV: $R^4=CH_3$; $R^5=R^6=R^7=R^8=R^9=H$; $R^{10}=OH$). The tar-like solid was dissolved in chloroform and extracted twice with aqueous solutions consisting of 300.0 ml of water and 12.0 ml of 50 percent aqueous sodium hydroxide. The two alkaline water layers were combined and slowly concentrated hydrochloric acid was added. At a pH of approximately 7 the solid which formed was collected by filtration and dried to obtain 5.25 g of 2-{2-hydroxy-4-N-methyl-N-[2-(2-pyridyl)ethyl]aminophenyl}carbonylbenzoic acid, a dark red-colored solid. The filtrate was adjusted to a pH of approximately 3.6 with concentrated hydrochloric acid and the solid which formed was collected by filtration, washed with water and dried to obtain 22.5 g of 2-{2-hydroxy-4-N-methyl-N-[2-(2-pyridyl)ethyl]aminophenyl}carbonylbenzoic acid, a pale pick-colored solid.

C. Slowly, 3.7 g (0.01 mole) 2-{2-hydroxy-4-N-methyl-N-[2-(2-pyridyl)ethyl]aminophenyl}carbonylbenzoic acid, prepared in a manner similar to that described in part B above, was added to 20.0 ml of 100 percent sulfuric acid. After the benzoic was dissolved completly, 2.1 g (0.01 mole) of 4-ethoxydiphenylamine was added slowly and when the addition was complete, 4 drops of 30 percent oleum was added. After approximately one hour of stirring at ambient temperature, the reaction mixture was poured slowly onto ice and the resulting mixture was adjusted to approximately pH 11.5 using 50 percent aqueous sodium hydroxide. Toluene and a small amount of benzyl trimethylammonium bromide were added to the mixture and the resulting mixture was maintained at reflux temperature for approximately six hours. After cooling to ambient temperature, the toluene layer was separated from the water layer and the water layer was extracted with a portion of fresh toluene. The two toluene layers were combined and concentrated under reduced pressure to obtain a viscous red-colored oil. The oil was purified by passing it through a silica gel packed chromatography column using ethylacetate as the carrier. The third fraction that was collected contained predominantly 2-anilino-6-{N-methyl N-[2-(2-pyridyl)ethyl]amino}fluoran (Formula III: $R=C_6H_5$; $R^1=R^2=R^5=R^6=R^7=R^8=R^9=H$; $R^4=CH_3$), a pale violet-colored solid which melted over the range 81° to 90° C. An infrared maximum appeared at 1754 cm$^{-1}$ (C=O;s). Nuclear magnetic resonance spectral analysis indicated that the solid contained approximately 93 percent of the desired product. A toluene solution of the product spotted on an acidic clay-coated paper and a phenolic resin-coated paper developed a green-colored image.

D. With stirring, 30.0 g (0.08 mole) of 2-{2-hydroxy-4-N-methyl-N-[2-(2-pyridyl)ethyl]aminophenyl}carbonylbenzoic acid, prepared in a manner similar to part B above, was added slowly to 150.0 ml of 100 percent sulfuric acid keeping the temperature under 37° C. Approximately twenty minutes after the last addition of benzoic acid, 18.2 g of 4-methoxy-2-methyldiphenylamine was added gradually keeping the temperature in the range of 20°-25° C. The reaction mixture was stirred at ambient temperature for approximately seventy-five minutes and then it was poured slowly onto ice with stirring. The pH of the resulting mixture was adjusted to approximately 12.5 with the gradual addition of 50 percent aqueous sodium hydroxide solution. The mixture was allowed to warm-up during the addition of the sodium hydroxide. The resulting aqueous mixture was extracted twice, each time with fresh toluene. At the interface between the aqueous and the toluene layers considerable solid was present which was isolated by filtration. Finally, the aqueous layer was extracted with methylene chloride. The solid was extracted four times with fresh hot ethyl acetate and the four ethyl acetate solutions were combined together. The ethyl acetate was removed under reduced pressure. The solid which formed was collected by filtration and dried to obtain 2.7 g of a light purple solid. The toluene solution was evaporated under reduced pressure to obtain a tar-like solid. The tar-like solid was dissolved with ethyl acetate, dried over solid potassium carbonate and the ethyl acetate was removed at reduced pressure. The solid which formed was collected to obtain 3.4 g of a purple-colored solid. The two solids were combined and ground in the presence of ethyl acetate, the solid collected by filtration, washed with ethyl acetate and dried to obtain 1.9 g of 2-anilino-3-methyl 6-{N-methyl-N-[2-(2-pyridyl)ethyl]amino}fluoran (Formula: III; $R=C_6H_5$; $R^1=R^5=R^6=R^7=R^8=R^9=H$; $R^2=R^4=CH_3$), a pale pink-colored solid which melted at 153°-160° C. The infrared spectrum showed a significant maximum at 1760 cm$^{-1}$(C=O;s). A toluene solution of the product spotted on an acidic clay coated paper and a phenolic resin coated paper develops a black-colored image.

EXAMPLE 17

A. With stirring a mixture of 44.0 g of 3-hydroxyaniline, 60.0 g of 2-vinylpyridine, 140.0 ml of methyl alcohol and 5.0 ml of glacial acetic acid was maintained at reflux temperature for approximately twenty-four hours. The methyl alcohol was removed by distillation and a mixture of water and toluene was added to the resultant residue. Three layers resulted. Sufficient 5 percent aqueous sodium hydroxide was added to adjust the water layer to approximately pH 7. The bottom oil layer was separated, and dried under reduced pressure to obtain a gummy solid which was triturated with hexane to obtain 69.0 g of N-[2-(2-pyridyl)ethyl]-3-hydroxyaniline(Formula V: $R^4=R^9=H$; $R^{10}=OH$), a pale tan solid which after being exposed to air turned into a taffy-like solid. The nuclear magnetic resonance spectrum was concordant with the assigned structure. The water layer was discarded. The toluene layer was washed first with water and then with saturated sodium chloride solution and evaporated to dryness under reduced pressure. The residue was recrystallized from a mixture of ispropanol and hexane to obtain 3.9 g of N-[2-(2-pyridyl)ethyl]-3-hydroxyaniline, a white solid which melted at 118°-120° C. A significant infrared maximum appeared at 1195 cm$^{-1}$(N—C;s). The nuclear magnetic resonance spectrum was consistent with the assigned structure.

B. A mixture of 22.0 g (0.148 mole) of phthalic anhydride, 32.0 g (0.148 mole) of N-[2-(2-pyridyl)ethyl]-3-hydroxyaniline and 150.0 ml of ethylene dichloride was maintained at reflux for approximately three hours with stirring. After cooling to ambient temperature the solid which formed was collected by filtration, washed first with a mixture consisting of the filtrate and 30.0 ml of isopropyl alcohol and then twice, each time with 25.0 ml of a mixture of 4 parts of ethylene dichloride and 1 part of isopropanol. The solid was dried to obtain 36.4 g of 2-{2-hydroxy-N-[2-(2-pyridyl)ethyl]aminophenyl} carbonylbenzoic acid (Formula IV: $R^4=R^5=R^6=R^7=R^8=R^9=H$; $R^{10}=OH$), a white solid which melted 168.6°-168.9° C. An infrared maximum appeared at 1700 cm$^{-1}$ (C=O;m). The nuclear magnetic resonance spectrum was in accord with the assigned structure.

EXAMPLE 18

Proceeding in a manner similar to that described in Example 11B above interacting 2-[2-hydroxy-4-(N-cyclohexyl-N-methyl)aminophenyl]carbonylbenzoic acid with N-[2-(2-pyridyl)ethyl]4-methoxy-2-methylaniline there is obtained 2-[2-(2-pyridyl)ethyl]amino-3-methyl-6-(N-cyclohexyl-N-methyl)aminofluoran (Formula II: $R^1=R^5=R^6=R^7=R^8=R^9=H$; $R^2=R^4=CH_3$; $R^3=C_6H_{11}$).

EXAMPLE 19

In a manner similar to that described in Example 11B above 2-(2-hydroxy-4-dibutylaminophenyl)carbonylbenzoic acid is interacted with N-[2-(2-pyridyl)ethyl]4-methoxy-2-methylaniline to obtain 2-[2-(2-pyridyl)e- thyl]amino-3-methyl-6-dibutylaminofluoran (Formula II: $R^1=R^5=R^6=R^7=R^8=R^9=H$; $R^2=CH_3$; $R^3=R^4=C_4H_9$).

EXAMPLE 20

Following the procedure described in Example 1B above 2-[2-hydroxy-4-(N-4-methylphenyl-N-ethyl-)aminophenyl]carbonylbenzoic acid is interacted with N-[2-(2-pyridyl)ethyl]4-methoxy-2-methylaniline to obtain 2-[2-(2-pyridyl)ethyl]amino-3-methyl-6-N-(4-methylphenyl)-N-ethylaminofluoran (Formula II: $R^1=R^5=R^6=R^7=R^8=R^9=H$; $R^2=CH_3$; $R^3=4\text{-}CH_3C_6H_4$; $R^4=C_2H_5$).

EXAMPLE 21

B. Benzyl chloride is interacted with 2-amino-6-{N-[2-(2-pyridyl)ethyl]-N-(methyl)}aminofluoran in the presence of potassium carbonate to obtain 2-dibenzylamino-6-{N-[2-(2-pyridyl)ethyl]-N-(methyl)}aminofluoran (Formula III: $R=R^1=C_6H_5CH_2$; $R^2=R^5=R^6=R^7=R^8=R^9=H$; $R^4=CH_3$).

It is contemplated that by following the procedures described in the foregoing examples but employing the appropriate 2-[2-$R^{10}$-4-(N-$R^3$-N-$R^4$)aminophenyl]carbonyl-3-$R^8$-4-$R^7$-5-$R^6$-6-$R^5$-benzoic acid with the appropriate N-[2-($R^9$-pyridyl)ethyl]-N-R-4-$R^{10}$-2-$R^2$-aniline, there will be obtained 2-{N-[2-($R^9$-pyridyl)ethyl]-N-R}amino-3-$R^2$-6-(N-$R^3$-N-$R^4$)amino-4'-$R^5$-5'-$R^6$-6'-$R^7$-7'-$R^8$-fluorans of Formula II, Examples 22–40, presented in Table A hereinbelow.

TABLE A

Fluorans of Formula II

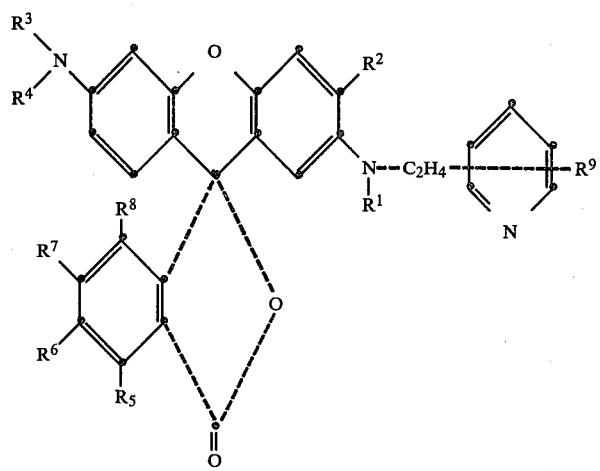

| Example No. | $R^1$ | $R^2$ | $R^3$ | $R^4$ | $R^5$ | $R^6$ | $R^7$ | $R^8$ | $R^9$ |
|---|---|---|---|---|---|---|---|---|---|
| 22 | $C_6H_{11}$ | H | $C_3H_7$ | $C_3H_7$ | Cl | Cl | Cl | Cl | H |
| 23 | $C_8H_{17}$ | Cl | $CH_3$ | $CH_3$ | H | H/COOC$_6$H$_{13}$ | H/COCC$_6$H$_{13}$ | H | $CH_3$ |
| 24 | 4-CH$_3$C$_6$H$_4$CH$_2$ | H | $C_4H_9$ | $C_4H_9$ | H | H | H | H | $CH_3$ |
| 25 | $C_6H_5$CHO | $C_3H_7$ | piperidino | | H | H/COOC$_4$H$_9$ | H/COOC$_4$H$_9$ | H | $C_2H_5$ |
| 26 | $C_3H_7$CHO | $C_2H_5$ | $C_3H_7$ | $C_3H_7$ | Br | Br | Br | Br | $CH_3$ |
| 27 | $C_6H_5$NHCHO | $CH_3$ | $C_3H_5$ | $C_2H_5$ | H | H/Cl | H/Cl | H | H |
| 28 | 4-CH$_3$C$_6$H$_4$SO$_3$ | H | $C_6H_5$ | $CH_3$ | H | H | H | H | $CH_3$ |
| 29 | 4-CH$_3$OC$_6$H$_4$CH$_2$ | Cl | 4-CH$_3$OC$_6$H$_4$CH$_2$ | $CH_3$ | H | H/COOC$_8$H$_{17}$ | H/COOC$_8$H$_{17}$ | H | $CH_3$ |
| 30 | $C_2H_5$CHO | Br | $C_6H_5$ | $C_2H_5$ | H | H | H | H | $CH_3$ |
| 31 | $C_5H_9$ | $CH_3$H | $C_4H_9$ | $C_4H_9$ | Cl | Cl | Cl | Cl | $CH_3$ |
| 32 | 2-BrC$_6$H$_4$CHO | H | $CH_3$ | $CH_3$ | H | H | H | H | $CH_3$ |
| 33 | 3-CH$_3$OC$_6$H$_4$CHO | $CH_3$ | $C_6H_5CH_2$ | $C_6H_5CH_2$ | H | H/NO$_2$ | H/NO$_2$ | H | H |
| 34 | H | Cl | morpholino | | H | H | H | H | $CH_3$ |
| 35 | 3-FC$_6$H$_4$CHO | $CH_3$ | 3-CH$_3$C$_6$H$_4$CH$_2$ | 4-CH$_3$C$_6$H$_4$CH$_2$ | H | H | H | H | H |
| 36 | 4-NO$_2$C$_6$H$_4$CHO | H | $CH_3$ | $CH_3$ | Cl | Cl | Cl | Cl | $CH_3$ |
| 37 | 2,4-(Cl)$_2$C$_6$H$_3$CHO | $CH_3$ | $C_6H_5$ | $C_2H_5$ | H | H/COOC$_{16}$H$_{33}$ | H/COOC$_{16}$H$_{33}$ | H | H |
| 38 | 4-CH$_3$C$_6$H$_4$CHO | H | $C_4C_9$ | $C_4H_9$ | H | H | H | H | H |
| 39 | $CH_3$ | $CH_3$ | 3-ClC$_6$H$_4$CH$_2$ | 3-ClC$_6$H$_4$CH$_2$ | H | H | H | H | H |
| 40 | $C_6H_5$SO$_3$ | H | $CH_3$ | $CH_3$ | H | H/COOC$_{12}$H$_{25}$ | H/COOC$_{12}$H$_{25}$ | H | $CH_3$ |

A. In a manner similar to that described in Example 16C above 2-{2-hydroxy-4-N-[2-(2-pyridyl)ethyl]-N-(methyl)aminophenyl}carbonylbenzoic acid is interacted 4-methoxyaniline to obtain 2-amino-6-{N-[2-(2-pyridyl)ethyl]-N-(methyl)}aminofluoran (Formula III:$R=R^1=R^2=R^3=R^4=R^5=R^6=R^7=R^8=R^9=H$; $R^4=CH_3$).

It is contemplated that by following the procedures described in the foregoing examples but employing the appropriate 2-{2-$R^1$-4-N-[2-($R^9$-pyridyl)ethyl]-N-$R^4$-aminophenyl}carbonyl-3-$R^8$-4-$R^7$-5-$R^6$-6-$R^5$-benzoic acid with the appropriate N-R-N-$R^1$-4-$R^{10}$-2-$R^2$-aniline, there will be obtained 2-N-R-N-$R^1$-amino-3-$R^2$-6-N-[2-($R^9$-pyridyl)ethyl]N-$R^4$-amino-4'-$R^5$-5'-$R^6$-6'-$R^7$-7'-$R^8$-fluoran of Formula III, Examples 41–54, presented in Table B hereinbelow.

TABLE B
Fluorans of Formula III

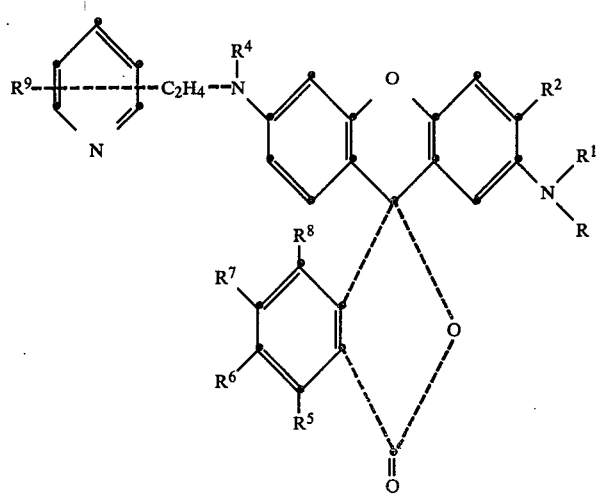

| Example No. | R | $R^1$ | $R^2$ | $R^4$ | $R^5$ | $R^6$ | $R^7$ | $R^8$ | $R^9$ |
|---|---|---|---|---|---|---|---|---|---|
| 41 | $C_8H_{17}$ | $C_8C_{17}$ | H | H | H | H | H | H | $CH_3$ |
| 42 | $C_6H_5$ | $CH_3$ | H | $CH_3$ | Cl | Cl | Cl | Cl | H |
| 43 | $4\text{-}CH_3C_6H_4CH_2$ | $4\text{-}CH_3C_6H_4CH_2$ | $CH_3$ | $C_2H_5$ | H | H | H | H | $CH_3$ |
| 44 | $2\text{-}ClC_6H_4$ | $CH_3$ | H | $CH_3$ | H | $H/COOC_4H_9$ | $H/COOC_4H_9$ | H | H |
| 45 | $C_4H_9$ | $C_4H_9$ | Cl | H | H | H | H | H | $CH_3$ |
| 46 | $2,4\text{-}(CH_3)_2C_6H_3$ | H | $CH_3$ | $CH_3$ | H | H | H | H | $CH_3$ |
| 47 | $C_6H_{11}$ | $C_2H_5$ | H | CHO | H | $H/NO_2$ | $H/NO_2$ | H | $CH_3$ |
| 48 | $C_8H_{15}$ | $CH_3$ | Br | H | Br | Br | Br | Br | H |
| 49 | $C_6H_5$ | H | $CH_3$ | $C_6H_5NHCO$ | H | H | H | H | $CH_3$ |
| 50 | $4\text{-}CH_3OC_6H_4CH_2$ | H | $CH_3$ | Cl | Cl | Cl | Cl | Cl | H |
| 51 | $2\text{-}FC_6H_4CH_2$ | $2\text{-}FC_6H_4CH_2$ | H | $C_4H_9$ | H | $H/Cl$ | $H/Cl$ | H | $CH_3$ |
| 52 | $C_6H_{13}$ | $C_6H_{13}$ | H | $CH_3$ | H | $H/COOC_8H_{17}$ | $H/COOC_8H_{17}$ | H | H |
| 53 | $3\text{-}NO_2C_6H_4CH_2$ | $3\text{-}NO_2C_6H_4CH_2$ | H | H | H | $H/COOC_{16}H_{33}$ | $H/COOC_{16}H_{33}$ | H | $CH_3$ |
| 54 | $2,4\text{-}(Cl)_2C_6H_3CH_2$ | $2,4\text{-}(Cl)_2C_6H_3CH_2$ | H | $CH_3$ | H | H | H | H | H |

It is contemplated that by following the procedures described in the foregoing examples but employing the 5-$R^6$-6-$R^5$-benzoic acids of Formula IV, Examples 55–64, presented in Table C hereinbelow.

TABLE C
Benzoic Acids of Formula IV

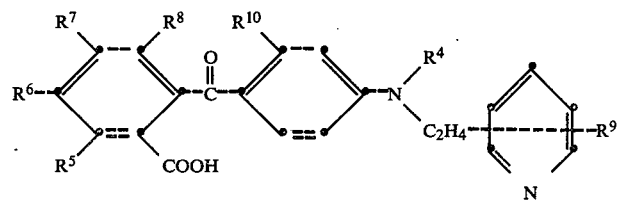

| Example No. | $R^4$ | $R^5$ | $R^6$ | $R^7$ | $R^8$ | $R^9$ | $R^{10}$ |
|---|---|---|---|---|---|---|---|
| 55 | H | Cl | Cl | Cl | Cl | $CH_3$ | OH |
| 56 | $C_6H_5CH_2$ | H | $H/NO_2$ | $H/NO_2$ | H | H | $OCH_3$ |
| 57 | $CH_3$ | H | $H/COOH$ | $H/COOH$ | H | H | OH |
| 58 | $C_4H_9$ | Br | Br | Br | Br | $C_2H_5$ | $OC_2H_5$ |
| 59 | $4\text{-}CH_3C_6H_4CH_2$ | $H/NO_2$ | H | H | $H/NO_2$ | H | OH |
| 60 | $3\text{-}NO_2C_8H_4CH_2$ | H | H | H | H | $C_4H_9$ | $OCH_3$ |
| 61 | $C_2H_5$ | H | $H/COOH$ | $H/COOH$ | H | H | $OC_3H_7$ |
| 62 | $2\text{-}CH_3OC_6H_4CH_2$ | Cl | Cl | Cl | Cl | $CH_3$ | OH |
| 63 | $2,4\text{-}Cl_2C_6H_3CH_2$ | H | $H/COOH$ | $H/COOH$ | H | $CH_3$ | OH |
| 64 | H | H | $H/NO_2$ | $H/NO_2$ | H | $CH_3$ | $OCH_3$ | appropriate N-[2-($R^9$-pyridyl)ethyl]-N-$R^4$-$R^{10}$-aniline with the appropriate 3-$R^5$-4-$R^6$-5-$R^7$-6-$R^8$-phthalic anhydride there will be obtained 2-{2-$R^{10}$-4-N-[2-($R^9$-pyridyl)ethyl]-N-$R^4$-aminophenyl}carbonyl-3-$R^8$-4-$R^7$-

It is contemplated that by following the procedures described in the foregoing examples but employing the appropriate N-$R^4$-3-$R^{10}$-aniline with the appropriate $R^9$-vinylpyridine, there will be obtained N-[2-($R^9$- pyridyl)ethyl]-N-$R^4$-3-$R^{10}$-anilines of Formula V, Examples 65–73, presented in Table D hereinbelow.

TABLE D

Anilines of Formula V

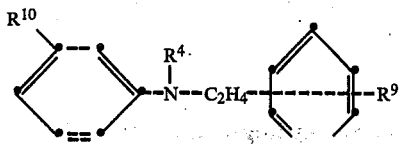

| Example No. | $R^4$ | $R^9$ | $R^{10}$ |
|---|---|---|---|
| 65 | H | $CH_3$ | OH |
| 66 | $C_6H_5CH_2$ | H | $OCH_3$ |
| 67 | $CH_3$ | H | OC |
| 68 | $C_4H_9$ | $C_2H_5$ | $OC_2H_5$ |
| 69 | 4-$CH_3C_6H_4CH_2$ | H | OC |
| 70 | 3-$NO_2C_6H_4CH_2$ | $C_4H_9$ | $OCH_3$ |
| 71 | $C_2H_5$ | H | $OC_3H_5$ |
| 72 | 2-$CH_3OC_6H_4CH_2$ | $CH_3$ | OH |
| 73 | 2,4-$Cl_2C_6H_3CH_2$ | $CH_3$ | OH |
| 74 | H | $CH_3$ | $OCH_3$ |

It is contemplated that by following the procedures described in the foregoing examples but employing the appropriate N-$R^1$-4-$R^{11}$-2-$R^2$-aniline with the appropriate $R^9$-vinylpyridine, there will be obtained-N-[2-($R^9$-pyridyl)ethyl]-N-$R^1$-4-$R^{11}$-2-$R^2$-anilines of Formula VI, Examples 74–84 presented in table E hereinbelow.

TABLE E

Anilines of Formula VI

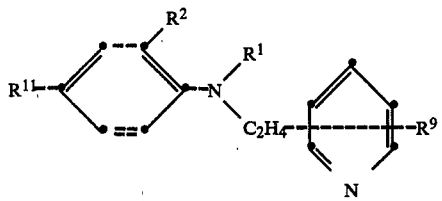

| Example No. | $R^1$ | $R^2$ | $R^9$ | $R^{11}$ |
|---|---|---|---|---|
| 74 | $CH_3$ | H | $CH_3$ | OH |
| 75 | $C_2H_5$ | Cl | H | $OCH_3$ |
| 76 | $C_6H_5CH_2$ | $CH_3$ | $C_2H_5$ | OH |
| 77 | $C_3H_7$ | Br | $CH_3$ | $OC_2C_5$ |
| 78 | $C_3H_7$ | Br | $CH_3$ | $OCH_3$ |
| 79 | 4-$CH_3OC_6H_4CH_2$ | H | $CH_3$ | OH |
| 80 | $CH_3$ | $CH_3$ | $C_3H_7$ | $OCH_3$ |
| 81 | 2-$ClC_6H_4CH_2$ | $C_4H_9$ | H | OH |
| 82 | 3-$NO_2C_5H_4CH_2$ | H | $CH_3$ | $OC_2H_5$ |
| 83 | 2,4-$Cl_2C_6H_3CH_2$ | $C_2H_5$ | H | OH |
| 84 | $C_2H_5$ | H | $C_2H_5$ | $OCH_3$ |

EXAMPLE 85

The use of the compounds of Formula I described in Examples 1 through 54, as color-forming components in pressure-sensitive microencapsulated copying systems is illustrated with reference to the product of Example 2, part B.

A. A mixture of 77.4 g of isopropylbiphenyl and 1.0 g of 2-[2-(2-pyridyl)ethyl]amino-3-methyl-6-diethylaminofluoran, prepared as described above in Example 2, part B, was heated to 100° C. until a clear solution was formed and then cooled to approximately 50° C. A second solution containing 60.5 ml of 275 Bloom gelatin dissolved in 38.0 ml of distilled water was heated at approximately 50° C. for about one hour.

B. The two solutions, the first containing the product and the isopropylbiphenyl, and the second containing the gelatin and the water were mixed and emulsified using a variable speed Hamilton-Beach No. 30 mixer equipped with a 1⅝ inch Cowles blade for approximately five minutes until the particle size of the suspended emulsion was approximately 2 microns at approximately 50° C. While maintaining the rapid agitation, the 45.0 g of gum arabic and 6.0 g of poly(methylvinylether maleic anhydride) were added and the pH adjusted to 9.0 with the addition of 10 percent aqueous sodium hydroxide. Slowly, 325.0 ml of distilled water at approximately 53° C. was added and the pH adjusted to 6.5 by the addition of 14 percent aqueous acetic acid. After five minutes of rapid agitation, the mixture was cooled to approximately 10° C. by means of an external ice-water bath and after 45 minutes of stirring 3.5 g of a twenty-five percent glutaraldehyde solution was added dropwise and agitation continued for 15 minutes. At this time, the Hamilton-Beach mixer was replaced with a conventional blade type laboratory agitator and the suspension was stirred overnight.

C. The stock microcapsule suspension prepared in part B above was coated on paper sheets to a thickness of approximately 0.0015 inch and the coated paper air dried. The paper thus coated with the microencapsulated colorless precursor was assembled as the top sheet in a manifold system by positioning the coated side in contact with the coated side of a commercially-available receiving sheet coated with a color developer of the electron-accepting type. More specifically, papers coated with a phenolic resin and with an acidic clay were employed in this test. An image was then drawn with a stylus on the top sheet bearing the microencapsulated colorless precursor on its reverse side, causing the affected microcapsules to rupture, thus allowing the solution of the colorless precursor held by said microcapsules to flow into contact with the color-developing substance on the receiving sheet, whereupon a black-colored image slowly formed on the resin-coated sheet and a black-colored image on the clay-coated sheet.

When evaluated in a pressure-sensitive microencapsulated carbonless duplicating paper prepared and tested as described above, the product of Example 1, part B, 2-[2-(2-pyridyl)ethyl]amino-6-diethylaminofluoran, produced a green-colored image on both the resin-coated sheet and the clay-coated sheet.

EXAMPLE 86

The utility of the compounds of Formula I whose preparations are described in the foregoing examples as color-forming components in thermal marking systems is illustrated by the incorporation and testing of the compound of Example 1B, 2-[2-(2-pyridyl)ethyl]amino-6-diethylaminofluoran, in a thermal-sensitive marking paper. The test paper was prepared by a procedure similar to that described in U.S. Pat. No. 3,539,375.

A. A mixture of 2.0 g of 2-[2-(2-pyridyl)ethyl]amino-6-diethylaminofluoran, 8.6 g of a ten percent aqueous solution of polyvinyl alcohol (approximately 99 percent hydrolyzed), 7.1 g of water and 31.6 g of 1/16 inch diameter zirconium grinding beads were charged into a container which was placed in a mechanical shaker. Shaking was effected for one hour. The zirconium beads were then removed by straining the mixture through a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 5.0 g of the slurry from part A and 45.0 g of the slurry from part B. The mixture was then uniformly coated onto sheets of paper at a thickness of approximately 0.0015 inch and the coated sheets air dried. The coated paper was tested by tracing a design on the coated side of the paper placed on a smooth flat surface with a stylus heated to approximately 135° C. A dark green-colored image corresponding to the traced design promptly developed.

We claim:

1. A 2-{2-$R^{10}$-4-N-[2-($R^9$-pyridyl)ethyl]-N-$R^4$-aminophenyl}carbonyl-3-$R^8$-4-$R^7$-5-$R^6$-6-$R^5$-benzoic acid having the formula

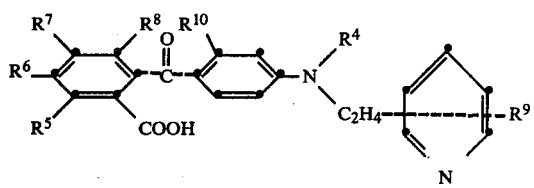

wherein:

$R^4$ represents hydrogen, non-tertiary $C_1$ to $C_4$ alkyl, benzyl or benzyl substituted in the benzene ring by one or two of halo, non-tertiary $C_1$ to $C_4$ alkyl, non-tertiary $C_1$ to $C_4$ alkyl, non-tertiary $C_1$ to $C_4$ alkoxy or nitro;

$R^5$, $R^6$, $R^7$ and $R^8$ each independently represent hydrogen, halo, or when $R^5$, $R^8$ and one of $R^6$ and $R^7$ represents hydrogen, the other of $R^6$ and $R^7$ represents COOH $R^9$ represents hydrogen, or non-tertiary $C_1$ to $C_4$ alkyl; and $R^{10}$ represents hydroxy or $C_1$ to $C_3$ alkoxy.

2. 2-{2-Hydroxy-4-N-[2-(2-pyridyl)ethyl]-N-methylaminophenyl}carbonylbenzoic acid according to claim 1.

* * * * *